(12) United States Patent
Verduzco et al.

(10) Patent No.: US 9,625,752 B1
(45) Date of Patent: Apr. 18, 2017

(54) RESPONSIVE LIQUID CRYSTAL ELASTOMERS FOR ENHANCED CELL SHEET ALIGNMENT

(71) Applicant: WILLIAM MARSH RICE UNIVERSITY, Houston, TX (US)

(72) Inventors: Rafael Verduzco, Houston, TX (US); Jeffrey G. Jacot, Houston, TX (US); Oluwatomiyin Adetiba, Houston, TX (US); Aditya Agrawal, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 38 days.

(21) Appl. No.: 14/330,691

(22) Filed: Jul. 14, 2014

Related U.S. Application Data

(60) Provisional application No. 61/846,362, filed on Jul. 15, 2013.

(51) Int. Cl.
G02F 1/13363 (2006.01)
C09K 19/38 (2006.01)
C12N 5/00 (2006.01)
G02F 1/1333 (2006.01)

(52) U.S. Cl.
CPC .... *G02F 1/133365* (2013.01); *C09K 19/3833* (2013.01); *C12N 5/0068* (2013.01); *C12N 2533/12* (2013.01); *C12N 2535/10* (2013.01); *Y10T 428/1086* (2015.01)

(58) Field of Classification Search
CPC ............. C12N 5/0068; C12N 2533/12; C12N 2533/30; C12N 2533/50; C12N 2533/52; C12N 2533/54; C12N 2535/10; C12N 2537/10; C09K 19/3833; G02F 2001/133633; Y10T 428/1086
See application file for complete search history.

(56) References Cited

U.S. PATENT DOCUMENTS

2005/0279730 A1* 12/2005 Miyake ................. B01L 3/0268
216/41
2007/0269848 A1* 11/2007 Abbott ................. C12N 5/0068
435/30

* cited by examiner

*Primary Examiner* — Shean C Wu
(74) *Attorney, Agent, or Firm* — Reed Smith LLP; Robert R. Riddle; Matthew S. Gibson

(57) ABSTRACT

Responsive, biocompatible substrates are of interest for directing the maturation and function of cells in vitro during cell culture. This can potentially provide cells and tissues with desirable properties for regenerative therapies. The present disclosure provides a scalable approach to attach, align and dynamically load cells on responsive liquid crystal elastomer (LCE) substrates. Monodomain LCEs exhibit reversible shape changes in response to cyclic stimulus, and when immersed in an aqueous medium on top of, for example, resistive heaters, shape changes are fast, reversible and produce minimal temperature changes in the surroundings.

7 Claims, 28 Drawing Sheets

FIG. 1A
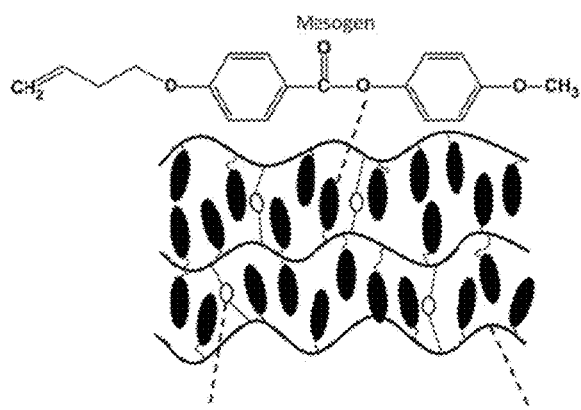
FIG. 1B
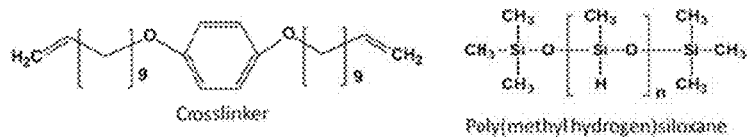
FIG. 2
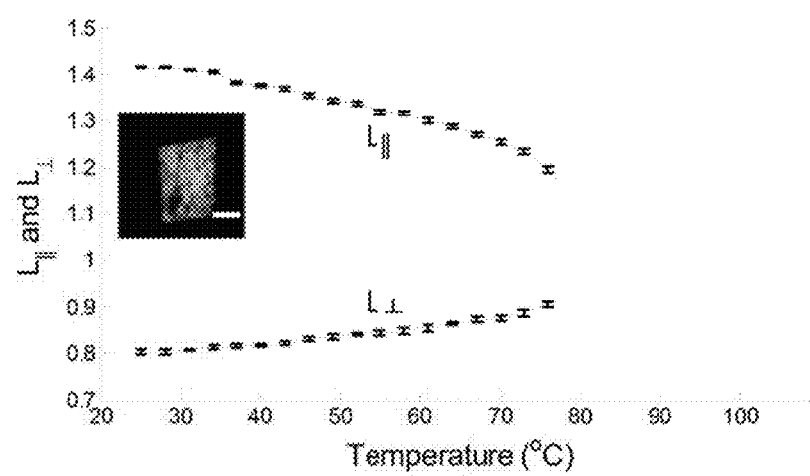

Figure 10
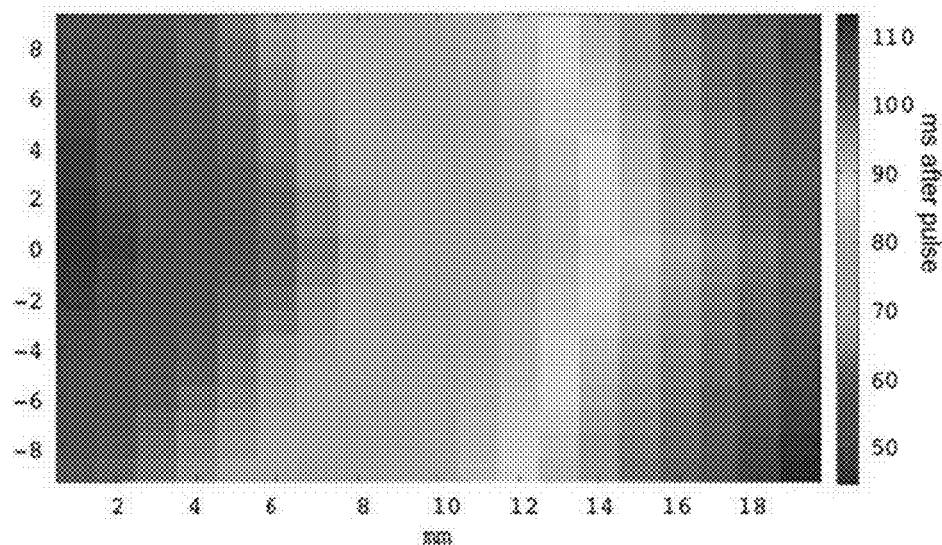
FIG. 11A                    FIG. 11B
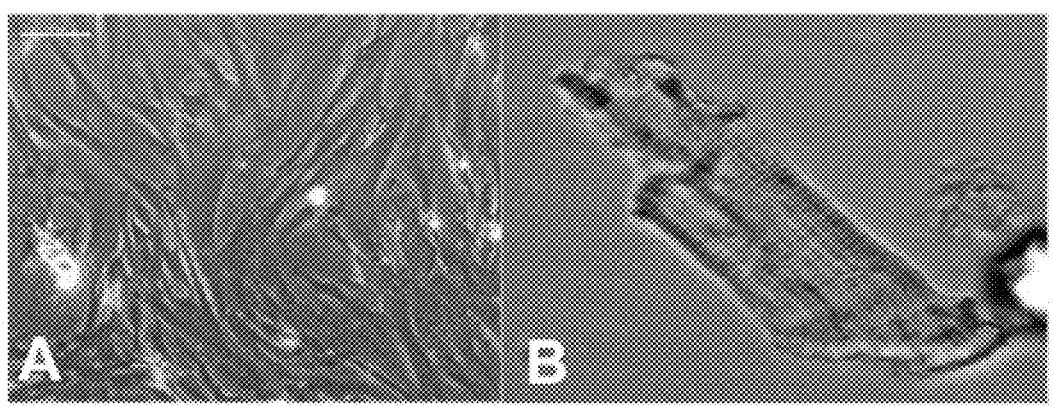

Monodomain LCE

LCE after immersion in CB/Toluene

LCE after immersion in CB/DCM

FIG. 18A
FIG. 18B
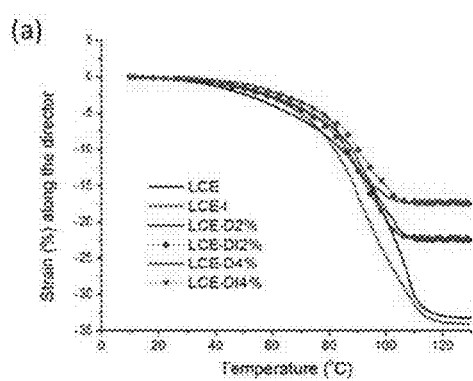
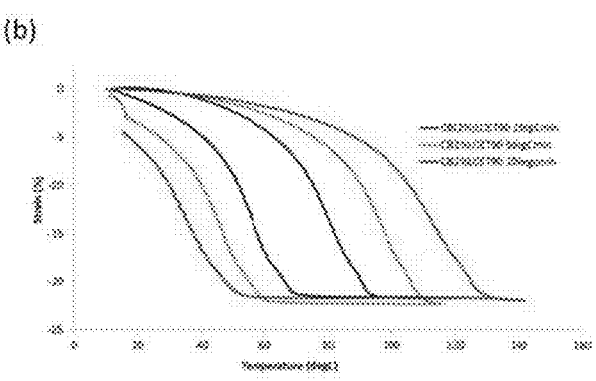
FIG. 19A
FIG. 19B
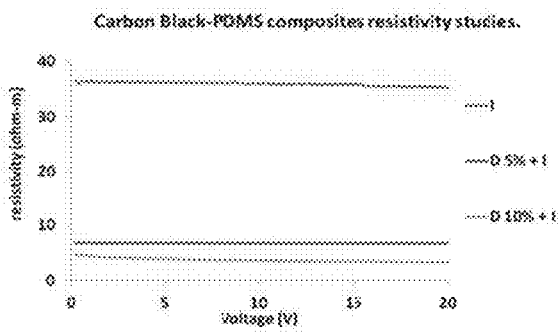
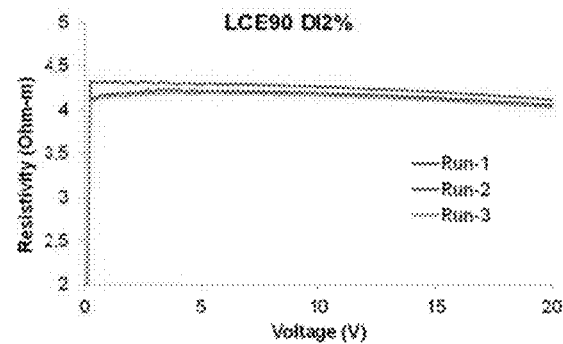

(a)           (b)           (c)

RESPONSIVE LIQUID CRYSTAL ELASTOMERS FOR ENHANCED CELL SHEET ALIGNMENT

CROSS REFERENCE TO RELATED APPLICATIONS

The present application claims priority to U.S. provisional application No. 61/846,362 filed Jul. 15, 2013.

STATEMENT OF GOVERNMENT INTEREST

This invention was made with government support under Award No. 1R21HL110330 awarded by National Institutes of Health. The government has certain rights in the invention.

BACKGROUND

A regenerative therapy for heat failure is layering sheets of muscle cells over a human heart for recovery of heart function. Current methods of developing muscular cell sheets include cells that can be patterned and aligned on surfaces through patterning of extracellular matrix attachment molecules or through micro- or nano-scale patterns in the scaffold itself, created through soft photolithography molding. Stretching of cardiomyocyte-plated materials can be accomplished through the use of external mechanical devices. Similarly, other cell types are enhanced for tissue regeneration and therapy through initial culture in the presence of mechanical stimuli. However, the methods typically employed require large amounts of space and are difficult to scale-up.

SUMMARY

The present disclosure generally relates to responsive liquid crystal elastomers and their use in culturing cells and processes for preparing such responsive liquid crystal elastomers ("LCE") and cell sheet cultures.

In one embodiment, a cell culture substrate is provided. The cell culture substrate comprises a liquid crystal elastomer layer comprising a liquid crystal mesogen and a polymer; and a cell-adhesion layer comprising a material selected from the group consisting of gold, polystyrene, collagen, fibronectin, laminin, and combinations thereof.

In another embodiment, a method for culturing cells is provided. The method comprises the steps of (a) culturing a plurality of cells on a liquid crystal elastomer substrate, wherein the liquid crystal elastomer substrate comprises a first shape characteristic; (b) applying a stimulus to the liquid crystal elastomer substrate sufficient to cause the liquid crystal elastomer substrate to change from the first shape characteristic to a second shape characteristic; and (c) allowing the liquid crystal elastomer substrate to change from the second shape characteristic to the first shape characteristic, wherein the method is performed while the cells are culturing.

In yet another embodiment, a cell culture system is provided. The cell culture system comprises: a power source; a stimulator in communication with the power source; and a liquid crystal elastomer substrate comprising a surface sufficient for cell adhesion and in contact with the stimulator, wherein the power source supplies power to the stimulator and is sufficient to induce a change in a shape characteristic of the liquid crystal elastomer substrate. In this and other embodiments, the system is adapted for use in a cell culture environment such that the stimulator may be immersed in culture media. The power source and stimulator may be, for example, a variable voltage source and a resistive heater, respectively. Furthermore, the power source and stimulator may comprise a single unit.

DRAWINGS

The patent or application file contains at least one drawing executed in color. Copies of this patent or patent application publication with color drawing(s) will be provided by the Office upon request and payment of the necessary fee. Some specific example embodiments of the disclosure may be understood by referring, in part, to the following description and the accompanying drawings.

FIG. 1A represents is a schematic that shows the structure of polysiloxane based side-chain LCE.

FIG. 1B depicts the optical microscopy images of LCE between crossed polarizers with the nematic director n oriented at (i) 0° C. and (ii) 45° C. with respect to crossed polarizers. The scale bars shown in this figure represent 50 µm.

FIG. 2 illustrates the shape change of LCE (10% crosslinking density) with temperature. L∥: normalized LCE dimension parallel to director; L⊥: normalized LCE dimension perpendicular to director. Normalization was done w.r.t corresponding isotropic lengths. The inset images show the shape change monitored at 35 and 90° C. under crossed polarized light. Scale bars represent 80 µm.

Figure 3A:
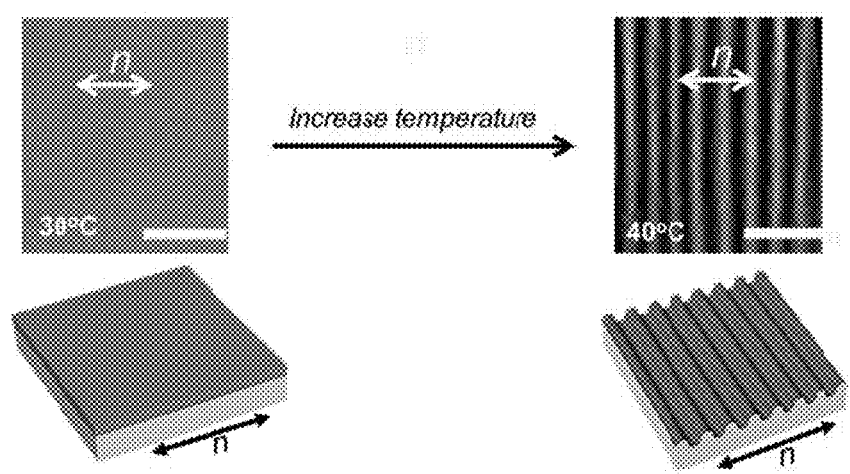

FIG. 3A depicts the optical microscopy images of the top surface of LCE bilayer samples prepared at 30° C. along with schematic images of the surface wrinkling instability. In this figure, n represents the orientation of LCE nematic director and all scale bars represent 10 µm.

Figure 3B:
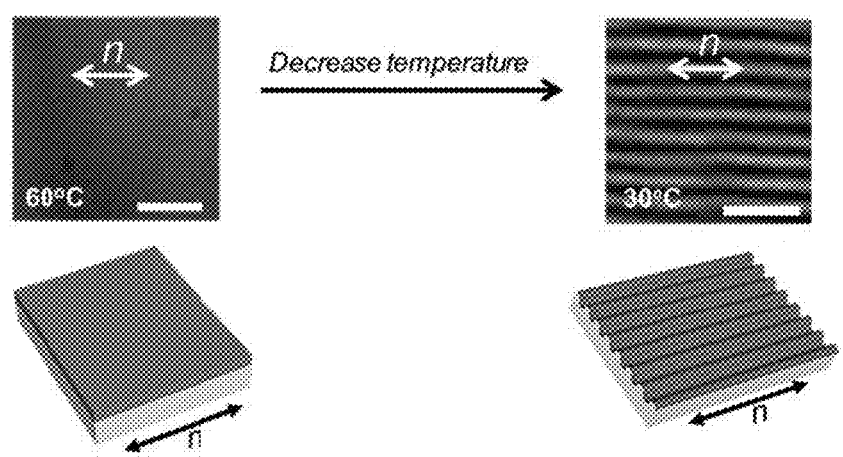

FIG. 3B depicts the optical microscopy images of the top surface of LCE bilayer samples prepared at 60° C. along with schematic images of the surface wrinkling instability. In this figure, n represents the orientation of LCE nematic director and all scale bars represent 10 µm.

Figure 4A:
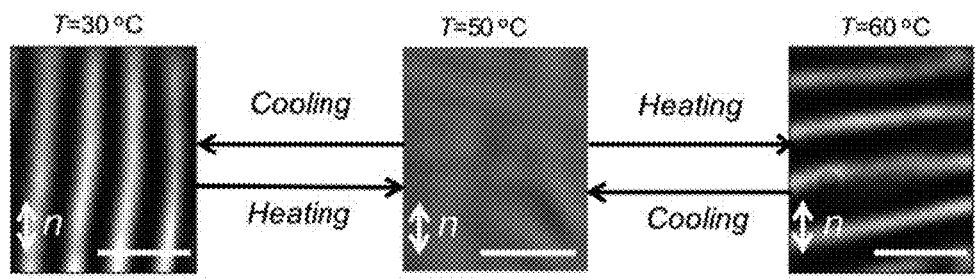

FIG. 4A depicts the optical microscopy images of the top surface of a PS-LCE bilayer prepared at 50° C. (scale bars: 5 µm). As shown, the wrinkles are re-oriented in a single sample by heating or cooling past the preparation temperature. In this figure, n represents the orientation of LCE nematic director.

Figure 4B:
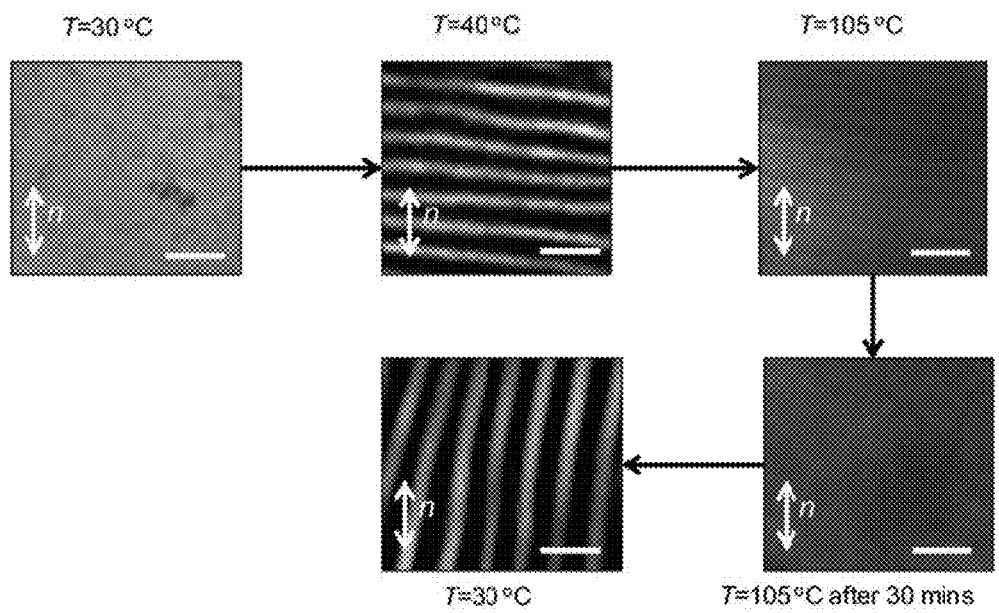

FIG. 4B depicts the optical microscopy images of the top surface of a PS-LCE bilayer prepared at 30° C. (scale bars: 10 µm). As shown, wrinkles are reoriented by heating to the Tg of PS, annealing the sample, and then cooling. In this figure, n represents the orientation of LCE nematic director.

Figure 5A:
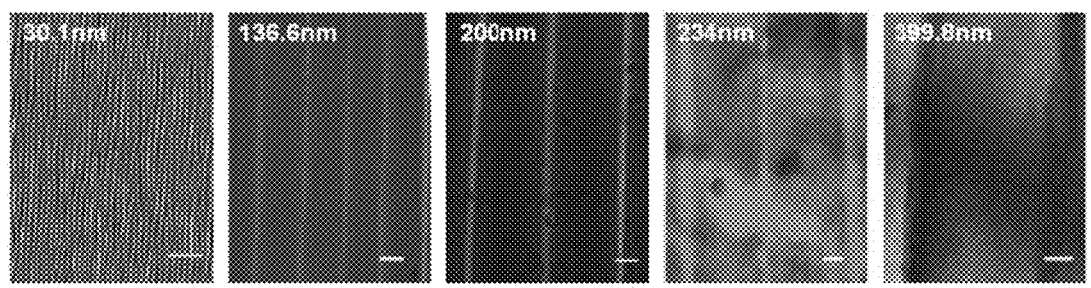
Figure 5B:
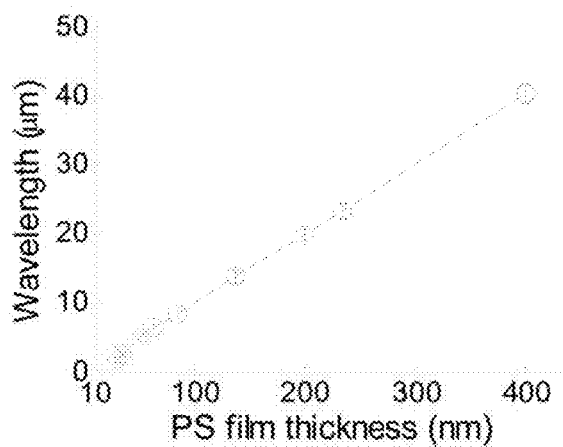
Figure 5C:
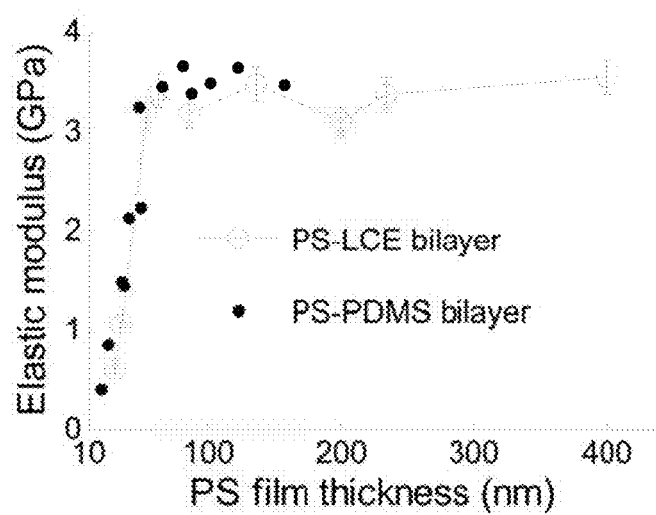

FIGS. 5A, 5B, and 5C depict 5A optical microscopy images showing wrinkling patterns of PS-LCE bilayers with varying PS film thicknesses, measured by spectroscopic ellipsometry and indicated by the number at the top of each image. FIG. 5B Dependence of wrinkling wavelength and FIG. 5C elastic modulus on the PS film thickness. The data points and error bars were evaluated by repeating each measurement six times. Scale bars represent 10 µm for all images shown. The experimental data for PS-PDMS bilayers shown were reported by Vogt et al. and were acquired by mechanically straining the bilayer sample.

Figure 6A:
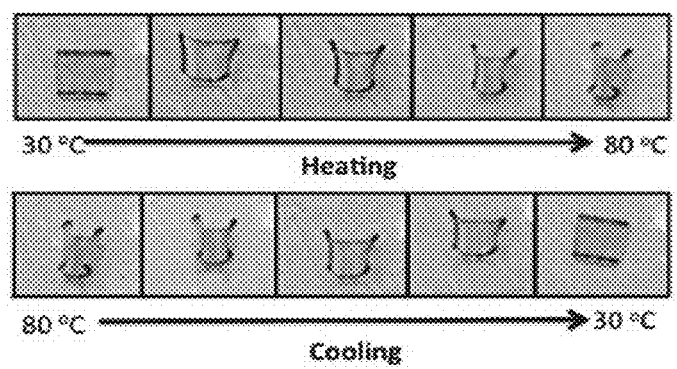

FIG. 6A depicts PS-LCE which reversibly curls with temperature. PS film and LCE substrate were 986 nm and 0.36 mm in thickness, respectively. Curvature was measured by taking images of the LCE sample during heating and cooling cycles and processing the images using Image J 1.440.

Figure 6B:
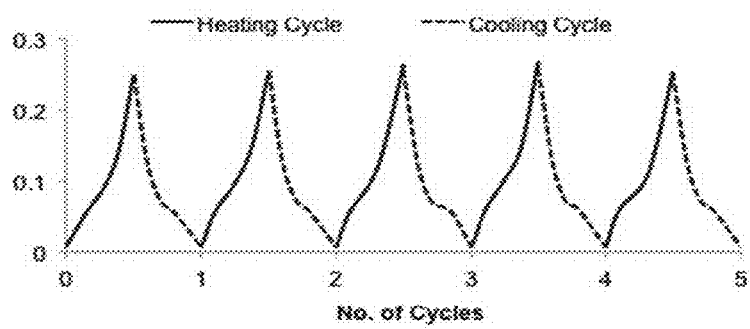

FIG. 6B depicts the curvature of PS-LCE bilayer as a function of number of heating and cooling cycles. PS film and LCE substrate were 986 nm and 0.36 mm in thickness, respectively. Curvature was measured by taking images of the LCE sample during heating and cooling cycles and processing the images using ImageJ 1.440.

Figure 7:
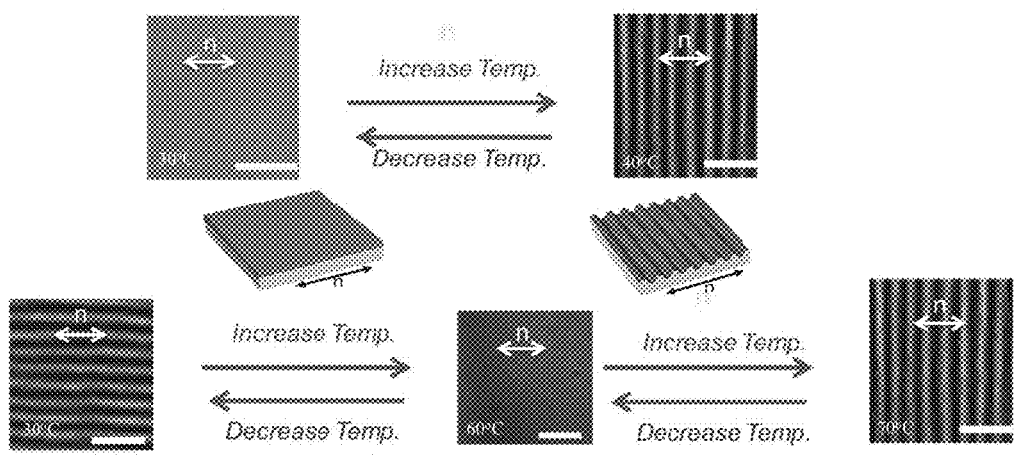

FIG. 7 is a schematic for reversible surface wrinkling in LCE bilayers using temperature as a stimulus. Surface wrinkles can be reversibly re-oriented or erased by increasing or decreasing the temperature. Scale bars are 10 µm.

Figure 8:
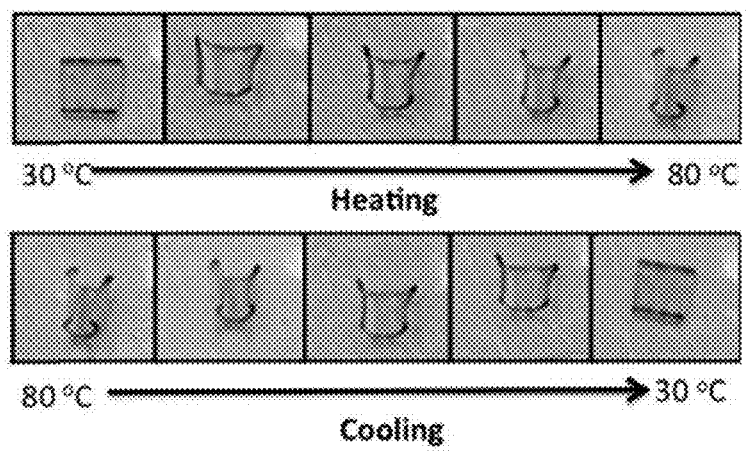
Figures 9A, 9B, 9C:
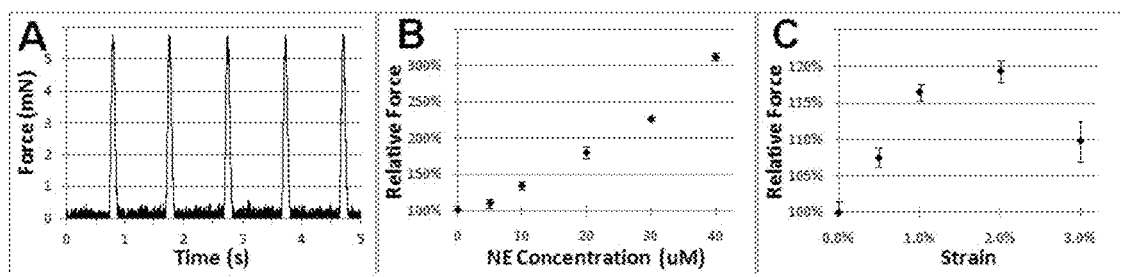
Figures 9D, 9E:
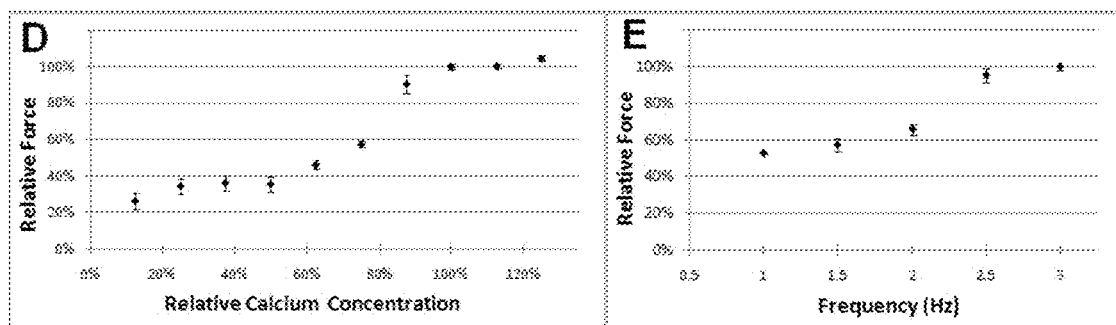

FIG. 8 is another depiction of a reversible curling in an LCE-PS bilayer.

FIGS. 9A, 9B, 9C, 9D, and -9E depict the direct measurement of physiologically-relevant force relationships in a study of adult rat myocardium in the lab of Dr. Jacot. (FIG. 9A) Unfiltered raw data of force generated by rat LV samples paced at 1 Hz using 0.8 V pulses with 1 ms durations. (FIG. 9B) Effect of adding a inotropic agent (in this case norepinephrine) to LV tissue paced at 1.5 Hz, 0.8 V, 1 ms. 100% force was 2.51 mN. (FIG. 9C) Dependence of force of rat LV tissue on the tissue prestrain, for tissue paced at 1.5 Hz, 0.8 V, 1 ms. 100% force was 4.51 mN and the original length of the sample was 10 mm. (FIG. 9D) Effect of calcium concentration (given as volume percent of 1.36 mM $Ca^{2+}$ in standard Tyrode's Solution) stimulated at 1.5 Hz, 0.8 V, 1 ms. 100% force was 5.76 mN. The samples were allowed to reach a steady beating pattern, and then 5 seconds of data were used to calculate average force and standard deviation. (FIG. 9E) Effect of pacing frequency on rat LV tissue paced at 0.8 V, 1 ms. 100% force was 10.5 mN.

FIG. 10 illustrates the measurement of a depolarization wave in a monolayer of neonatal rat ventricular myocytes labeled with the voltage sensitive dye Di-8-ANEPPS, stimulated by a 1V biphasic pulse from a microelectrode placed at location 0,0 (in the center left of the image) and imaged with a photo-multiplier tube over an array of points. The image is color coded for the arrival time of depolarization after the pulse.

FIGS. 11A and 11B illustrate cultured human cardiomyocytes from human right ventricular outflow tract cultured for 14 days in media M199 plus hormone T3 (FIG. 11A). Close up of a single myocyte reveals maintenance of striated morphology in some cells (FIG. 11B).

Figure 12A:
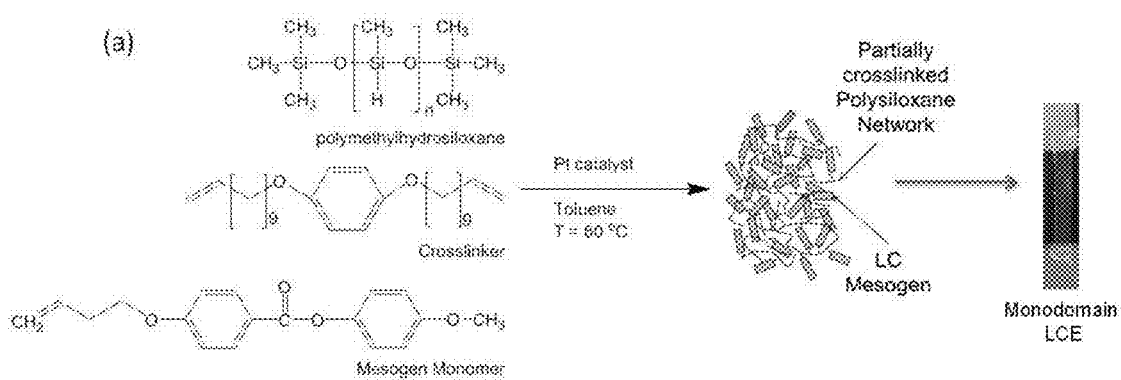
Figure 12B:
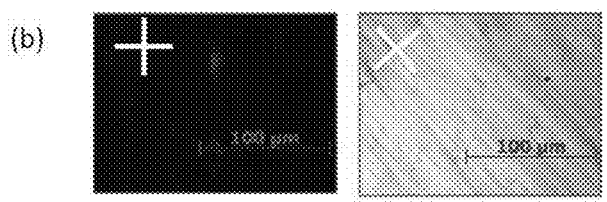
Figure 12C:
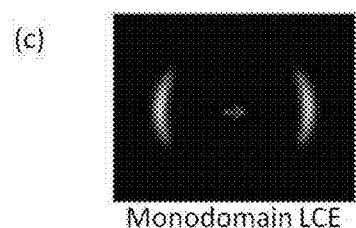

FIGS. 12A, 12B, and 12C depict the Monodomain LCE synthesis. (FIG. 12A) two step synthesis of monodomain LCEs (FIG. 12B) polarizing optical microscopy images and (FIG. 12C) 2D wide angle X-ray diffraction studies depicting uniform alignment of mesogens within LCE matrix.

Figure 13A:
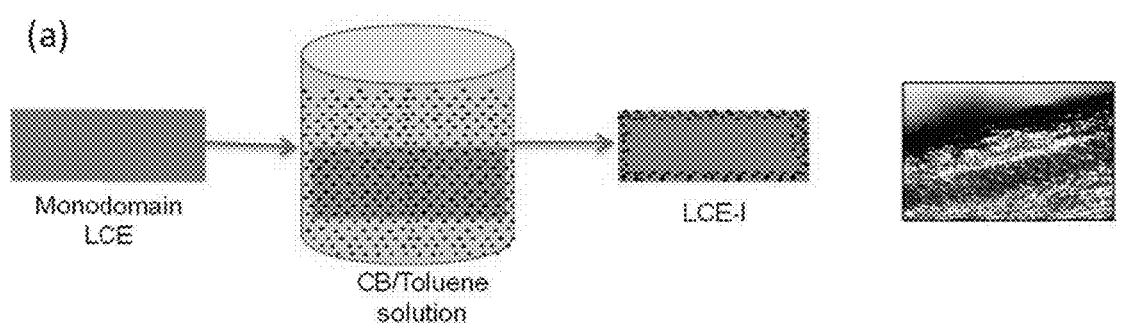
Figure 13B:
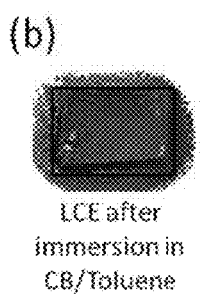
Figure 13C:
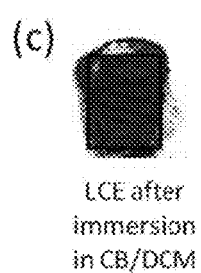

FIGS. 13A, 13B, and 13C are schematics of the CB-LCE via immersion (I) approach. (FIG. 13A) synthesis scheme of CB-LCE composite via immersion approach. Surface texture of LCE when immersed in (FIG. 13B) toluene and (FIG. 13C) dichloromethane. Boundary of LCE is highlighted for better visualization.

Figure 14:
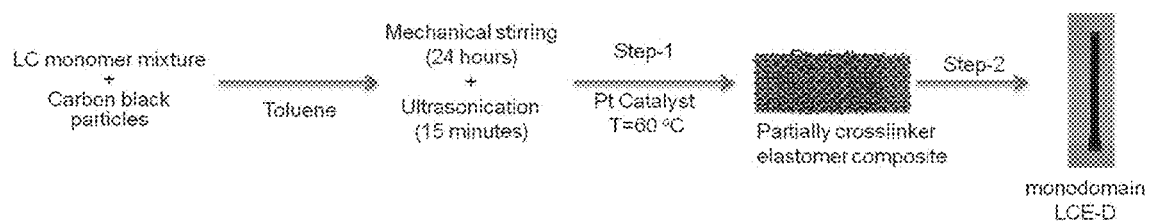

FIG. 14 is a schematic of the CB-LCE via dispersion (D) approach.

Figure 15:
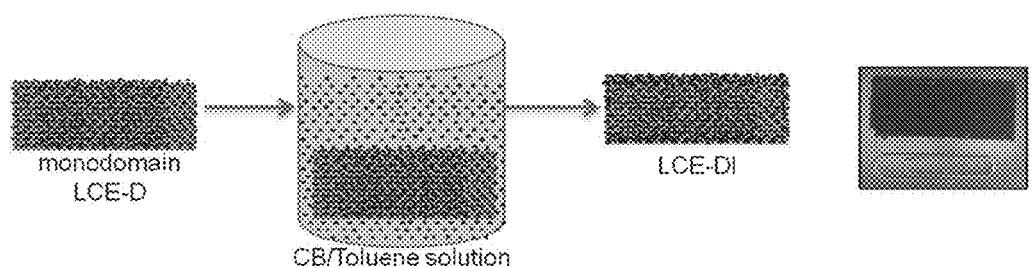

FIG. 15 is a schematic of the CB-LCE via immersion+dispersion (DI) approach.

Figure 16:
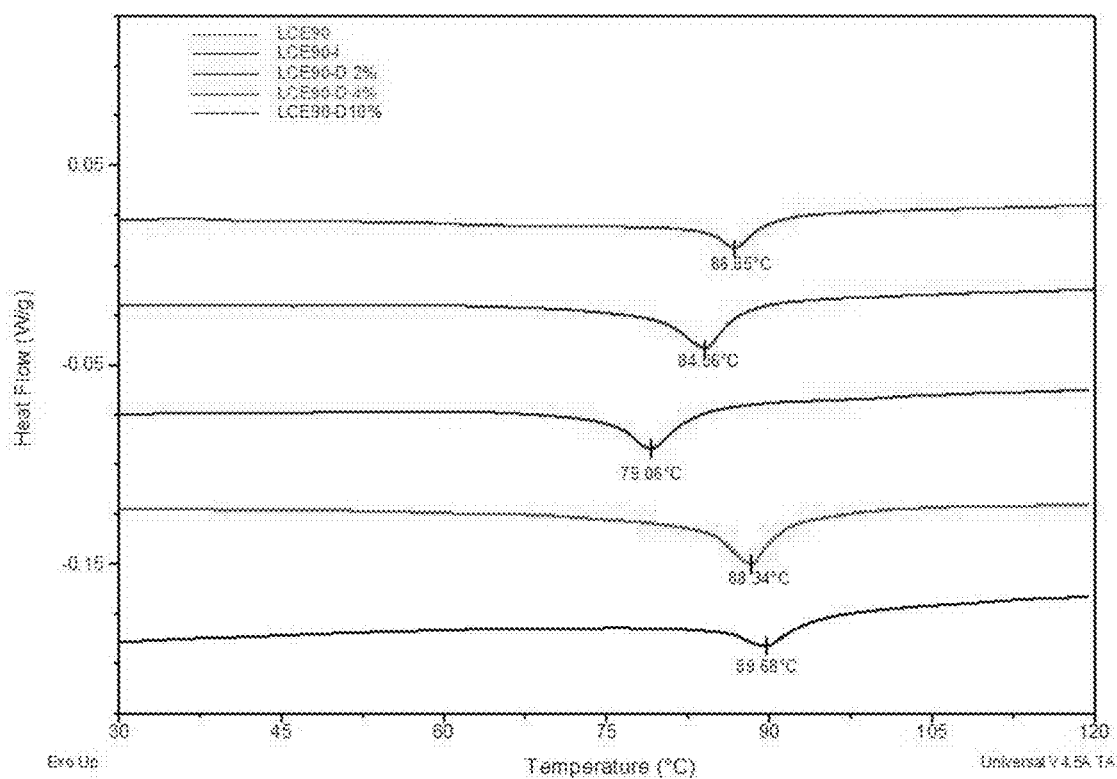

FIG. 16 depicts an estimation of nematic-isotropic (TNI) transition behavior of various CB-LCE composites via differential scanning calorimetry.

Figure 17:
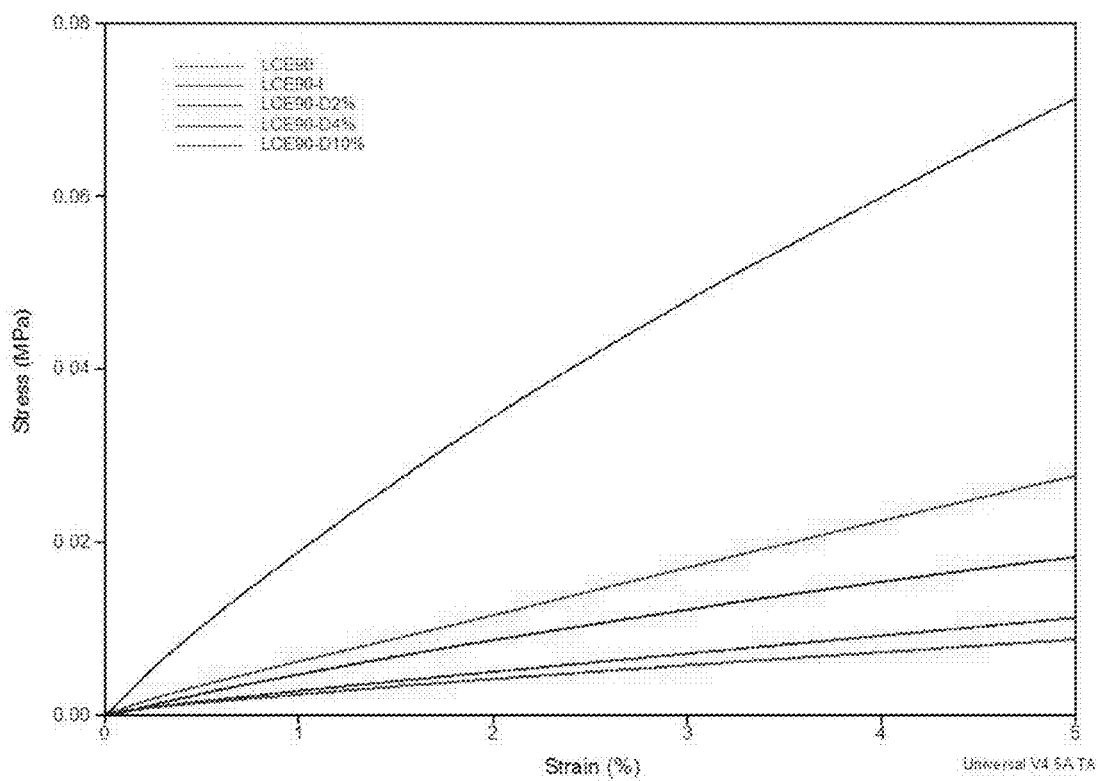

FIG. 17 depicts an estimation of elastic modulus of CB-LCE composites via DMA-Q800.

FIGS. 18A and 18B are the (FIG. 18A) thermal responses of different CB-LCE composites. Measurements were conducted using DMA-Q800 at a heating rate of 5° C./min. (FIG. 18B) effect of heating or cooling rate on the thermal response of CB-LCE composites.

FIGS. 19A and 19B are (FIG. 19A) comparisons of resistivity of CB-PDMS composites prepared via immersion and immersion+dispersion approach. (FIG. 19B) resistivity of CB-LCE composite prepared via immersion+dispersion approach.

Figure 20:
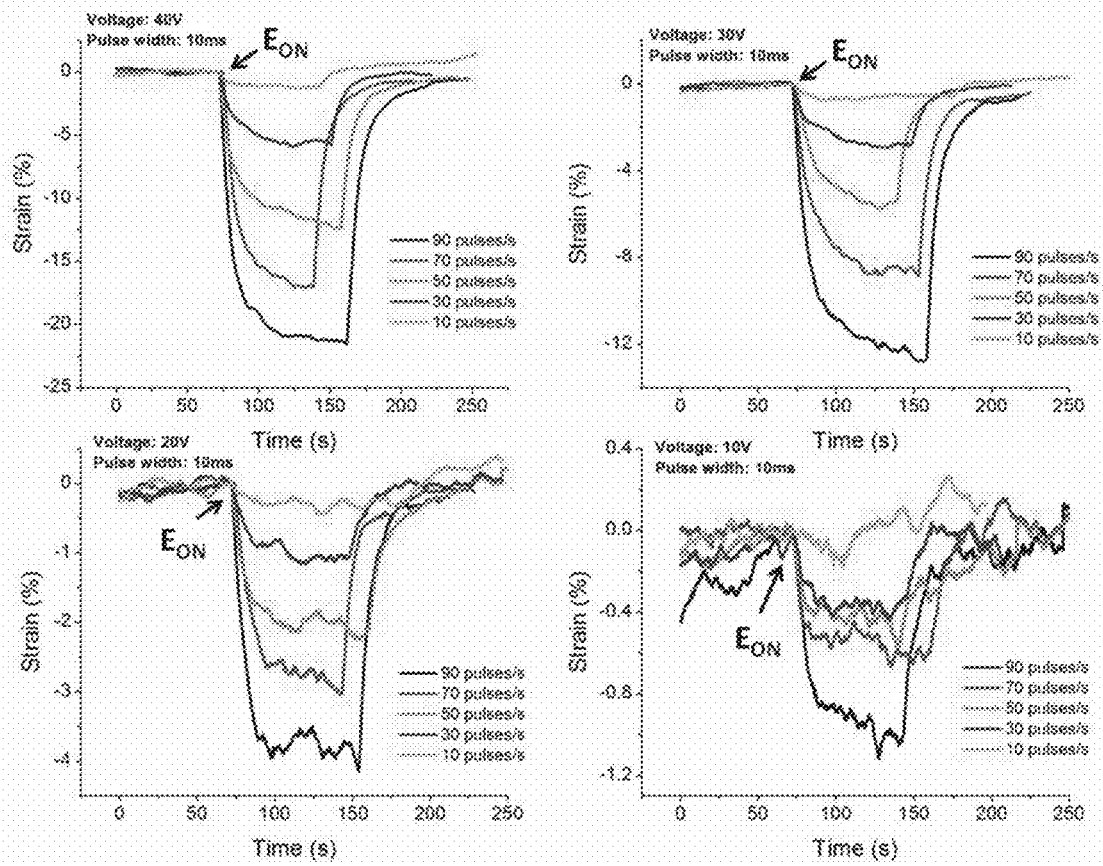

FIG. 20 illustrates the electromechanical response of CB-LCE composite prepared via immersion+dispersion approach as a function of applied voltage, frequency and pulse width. Contraction of LCE composite along the nematic director was recorded using DMA-Q800. Electric field was applied using Myopacer.

Figure 21:
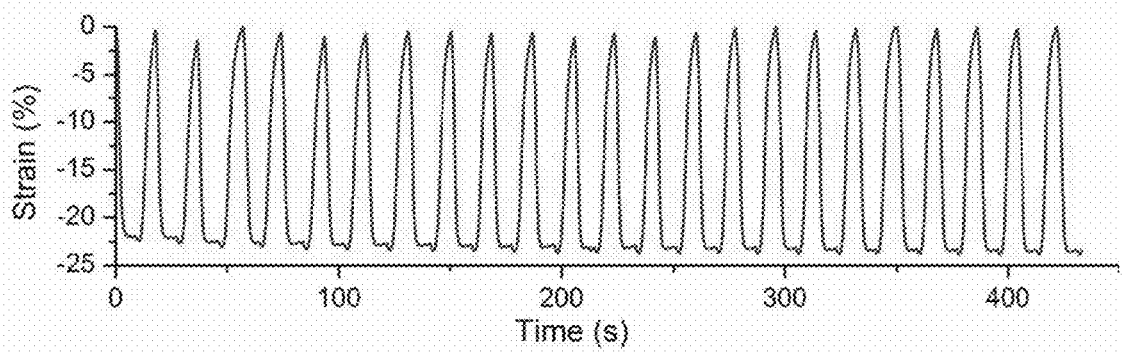

FIG. 21 depicts the reversible electromechanical response of CB-LCE composite prepared via immersion+dispersion approach. Contraction and expansion of LCE composite along the nematic director was recorded under applied electric field of 40V, 90 Hz and 10 ms pulse width.

Figure 22:
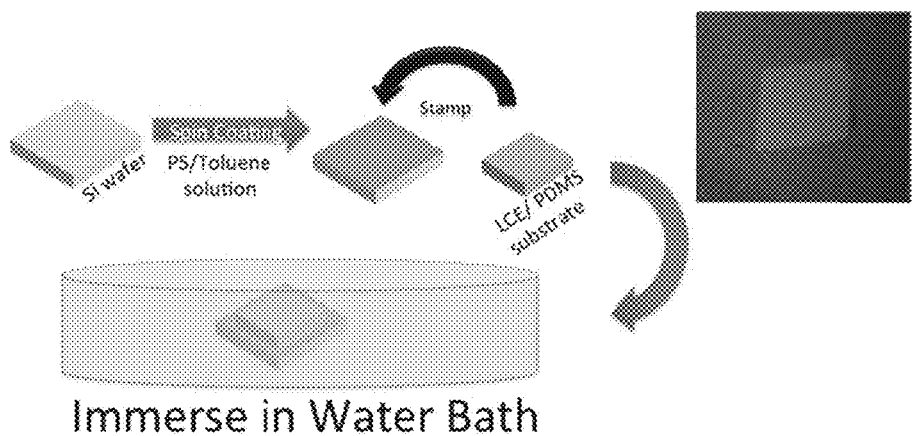

FIG. 22 is a schematic depiction of synthesis of PS-LCE or PS-PDMS bilayer via film transfer technique.

Figure 23:
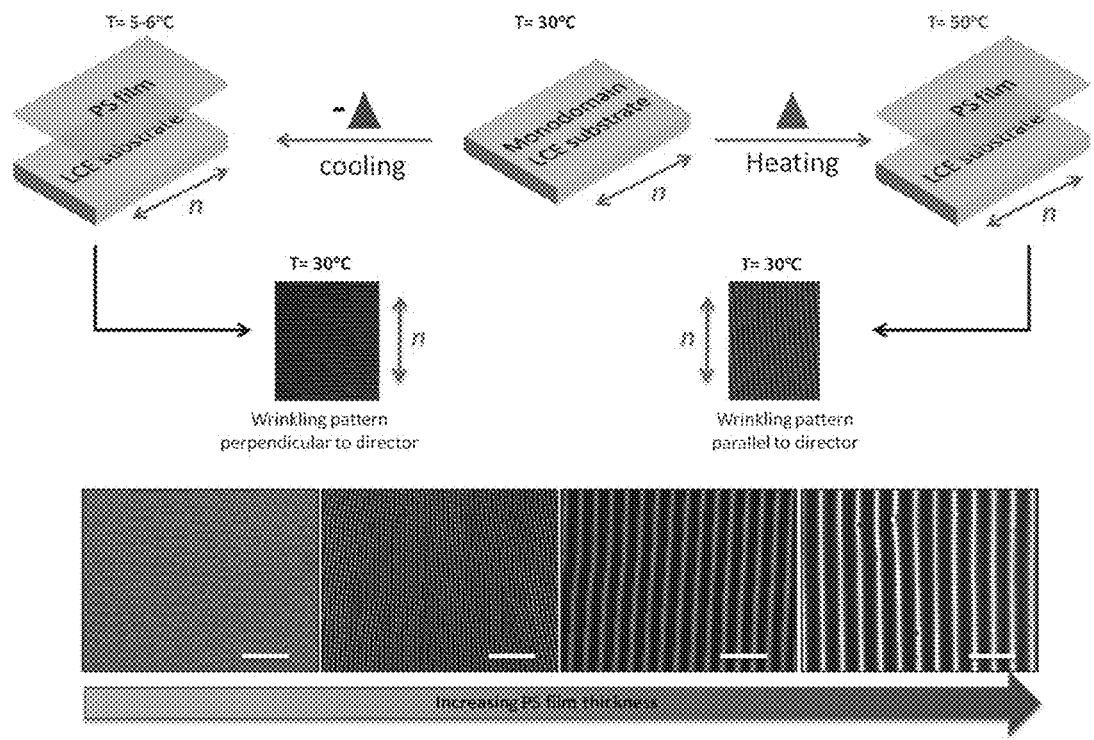

FIG. 23 illustrates a synthesis scheme of PS-LCE bilayers with uniformly aligned wrinkling pattern parallel and perpendicular to the nematic director.

Figure 24:
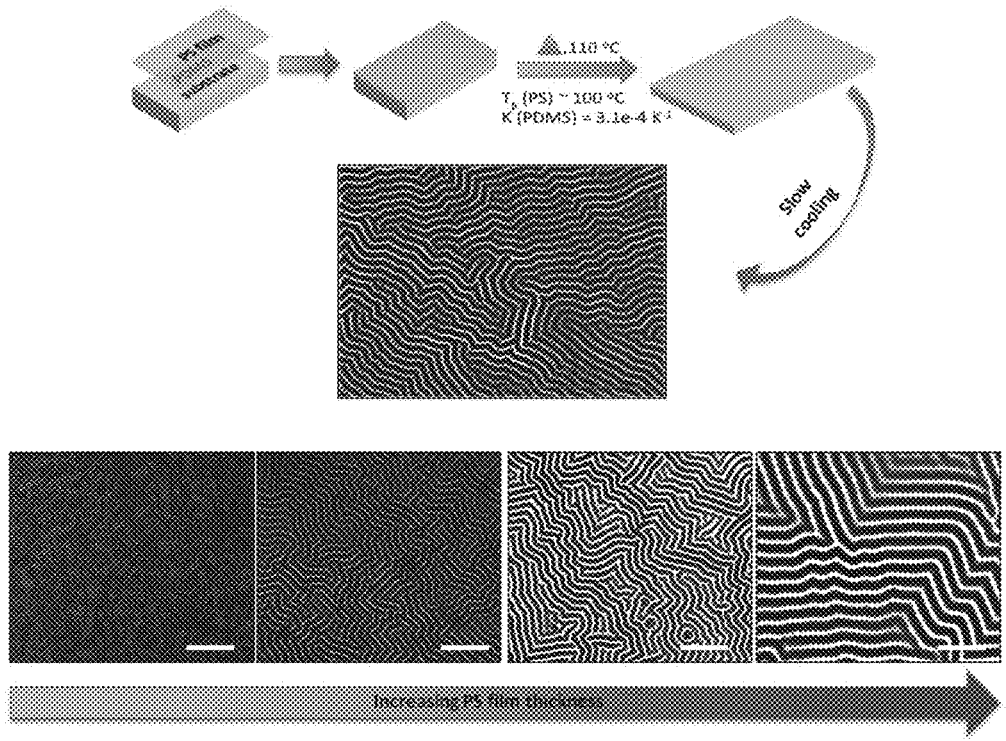

FIG. 24 illustrates a synthesis scheme of PS-PDMS bilayers with random wrinkling pattern.

Figure 25:
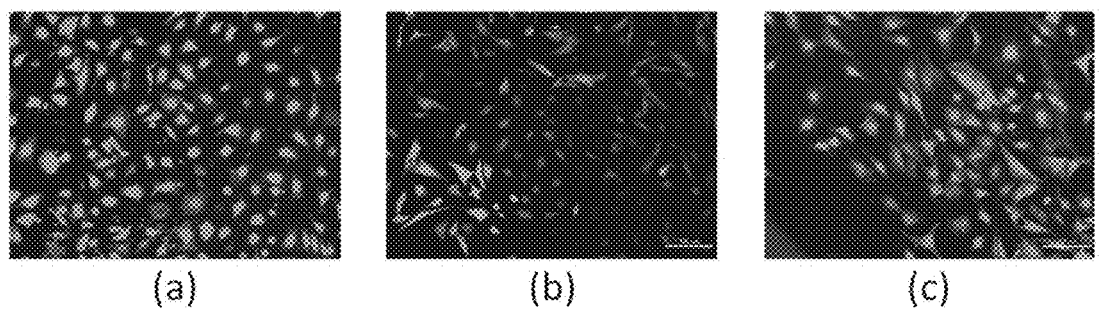

FIGS. 25A, 25B, and 25C depict cell culture images using PS-LCE bilayer substrate with (FIG. 25A) flat (FIG. 25B) random and (FIG. 25C) aligned wrinkling topography. The red arrow shows the direction of the wrinkling pattern in align sample. The cells were obtained from neonate (1 day old) Sprague-Dawley rat ventricular cardiomyocyte.

Figure 26:
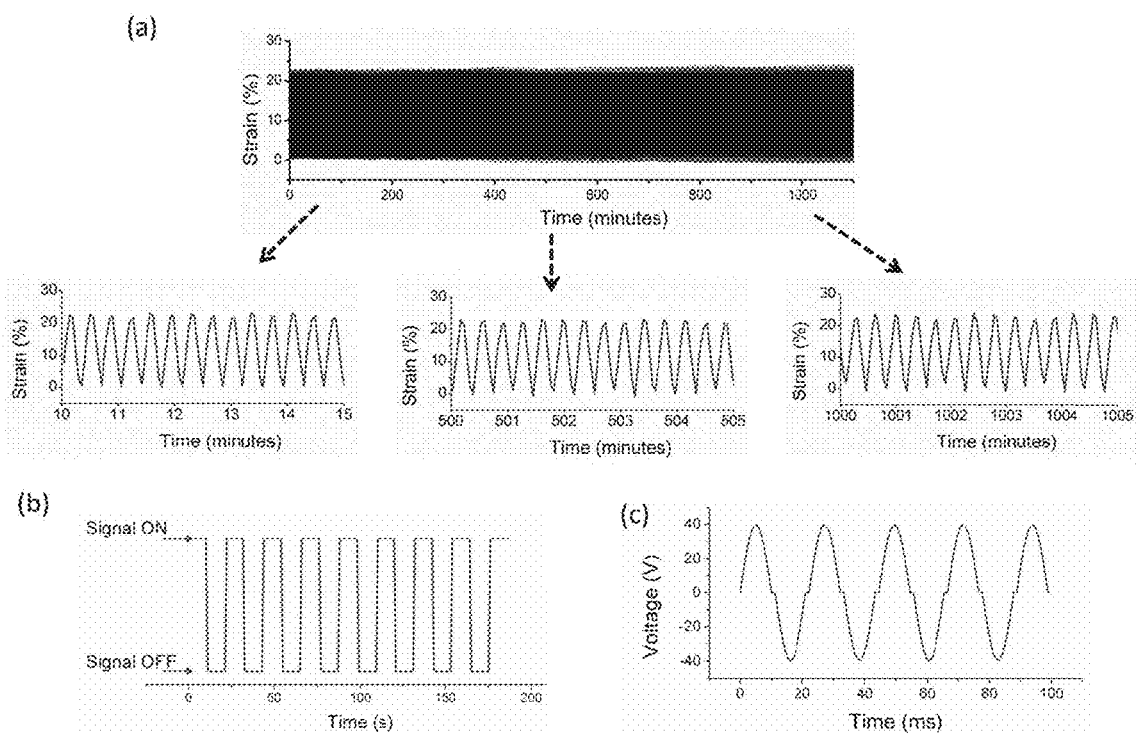

FIGS. 26A, 26B, and 26C depict graphs showing reversible electromechanical response of CB-LCE composite.

Figure 27:
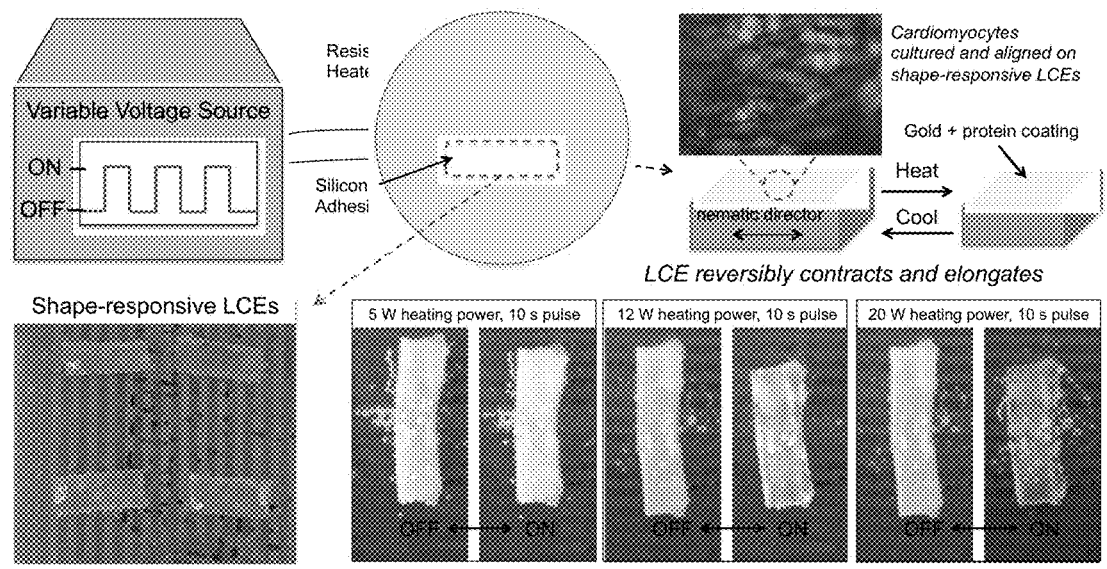

FIG. 27 depicts one embodiment of a dynamic cell culture system of the present disclosure (top) and photographs of LCEs on resistive heaters (bottom). A variable voltage supplied to the resistive heaters resulted in cyclic heating of the LCE substrates. The LCE substrates and resistive heaters were fully covered by culture media, and LCEs were held in place by a medical grade silicone adhesive. The petri dish and culture media resided in an incubator maintained at 37° C. and 5% CO2. For the images on the bottom-right side, the same LCE was analyzed at different heating powers and at a 10 s pulse duration (10 s on, 10 s off). The LCE was held in place by silicone adhesive. Images were taken after 10 min of cyclic heating for equilibration, and the LCE sample shown was approximately 9 mm in length.

Figure 28:
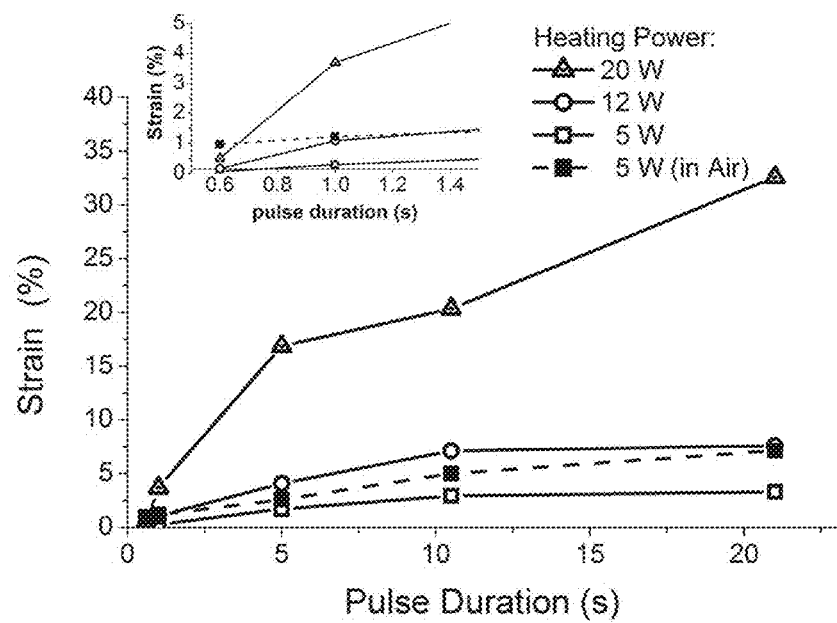

FIG. 28 illustrates the response of LCEs to cyclic on/off heating pulses at varying heating powers. Reversible strain was determined by measuring the maximum and minimum sample lengths during heat cycling. All samples were analyzed in water, except where indicated. The inset shows the strain measured for pulse durations shorter than 1.5 s.

Figure 29:
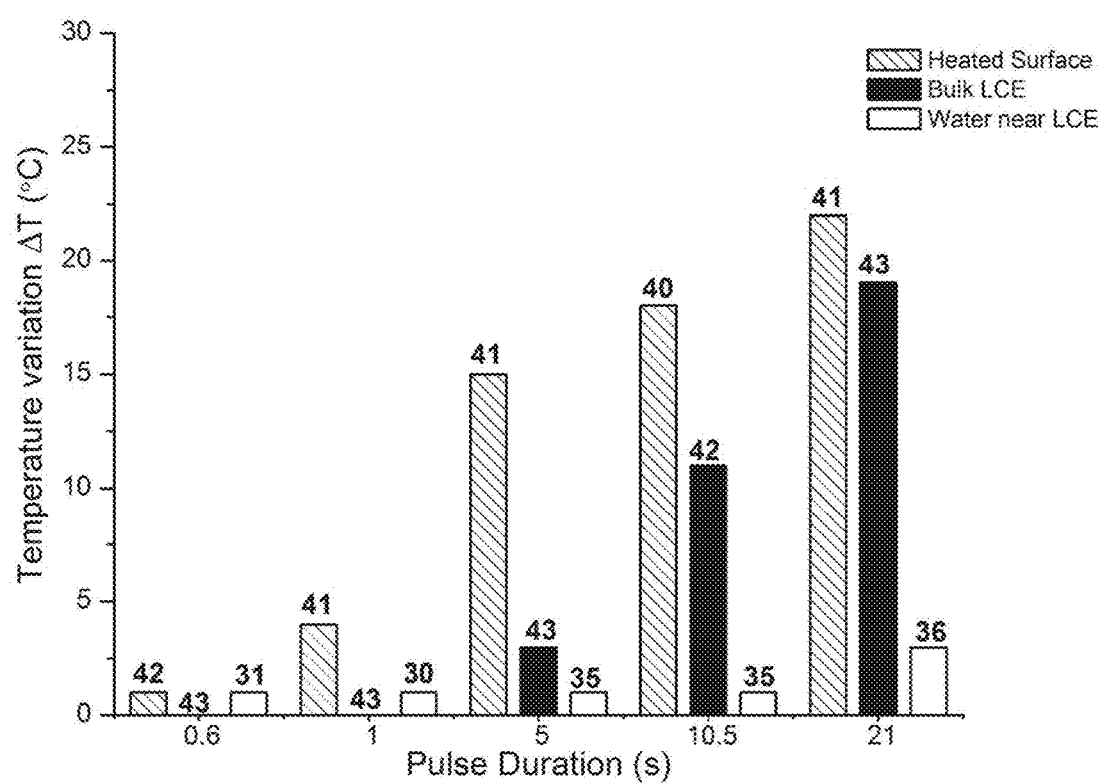

FIG. 29 illustrates temperature variation near the surface of the resistive heater, in the bulk LCE, and near the LCE surface for 12 W heating power. The values above each bar indicate the average temperature (° C.) for each case. All samples were allowed to equilibrate for at least 10 min under cyclic heating. The ambient temperature was approximately 25° C.

Figure 30:
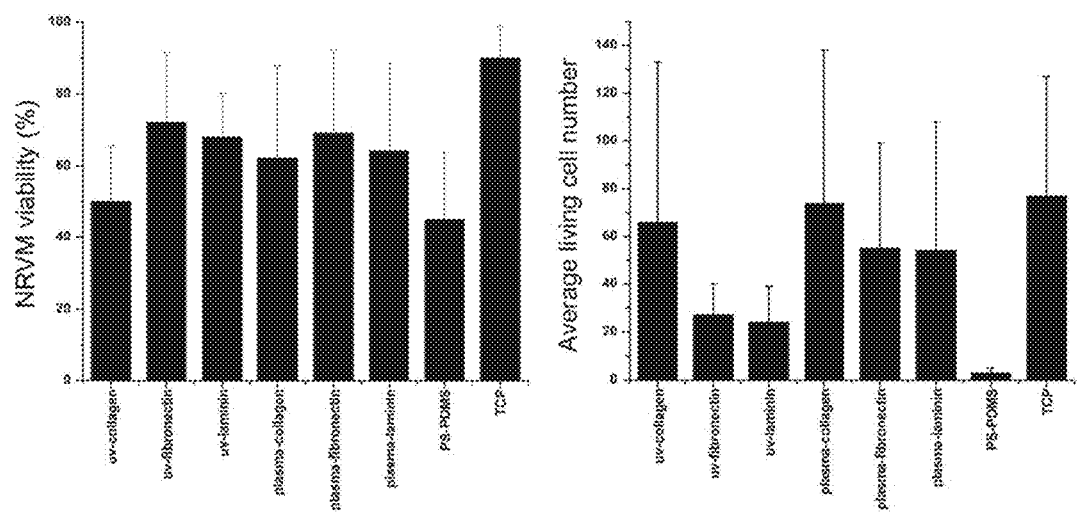

FIG. 30 illustrates NRVM viability and total number of live cells attached on PDMS-PS elastomers with different surface treatments. Three proteins and two cleaning procedures were tested. Tissue-culture plastic (TCP) and bare untreated PS-PDMS served as positive and negative controls, respectively.

Figure 31:
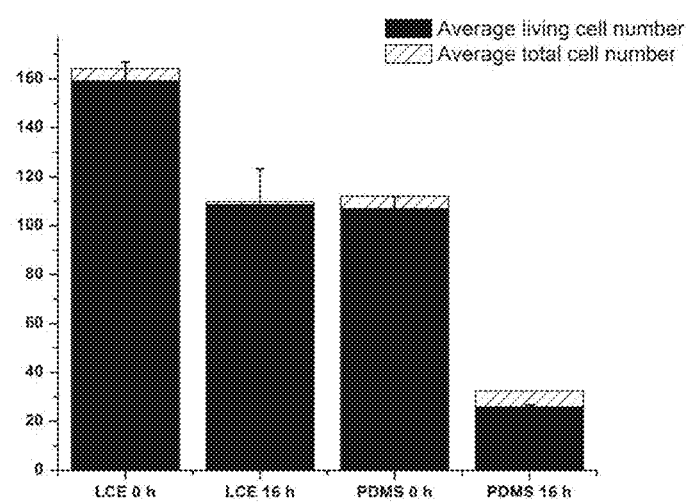

FIG. 31 illustrates NRVM live and total cell numbers on surface-modified LCE and PDMS samples. All elastomers were modified through deposition of a 30 nm gold layer followed by UV-ozone cleaning and deposition of collagen. Collagen was deposited either immediately after UV-ozone treatment (0 h) or 16 h after UV-ozone treatment. Standard deviations are for living cell numbers.

Figure 32:
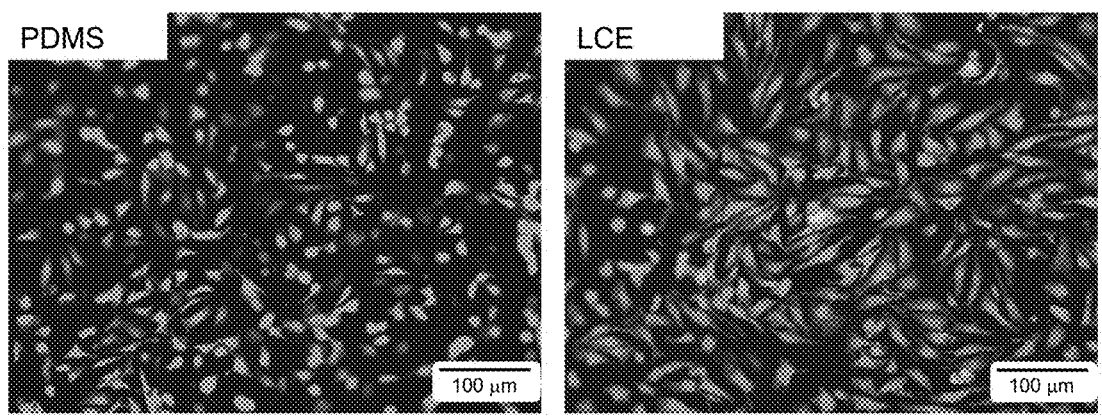

FIG. 32 illustrates Calcein AM stained images of cardiomyocytes on PDMS and LCE. Surfaces were treated by gold deposition and collagen in both cases. Live cells were pseudocolored green and dead cells red.

Figure 33:
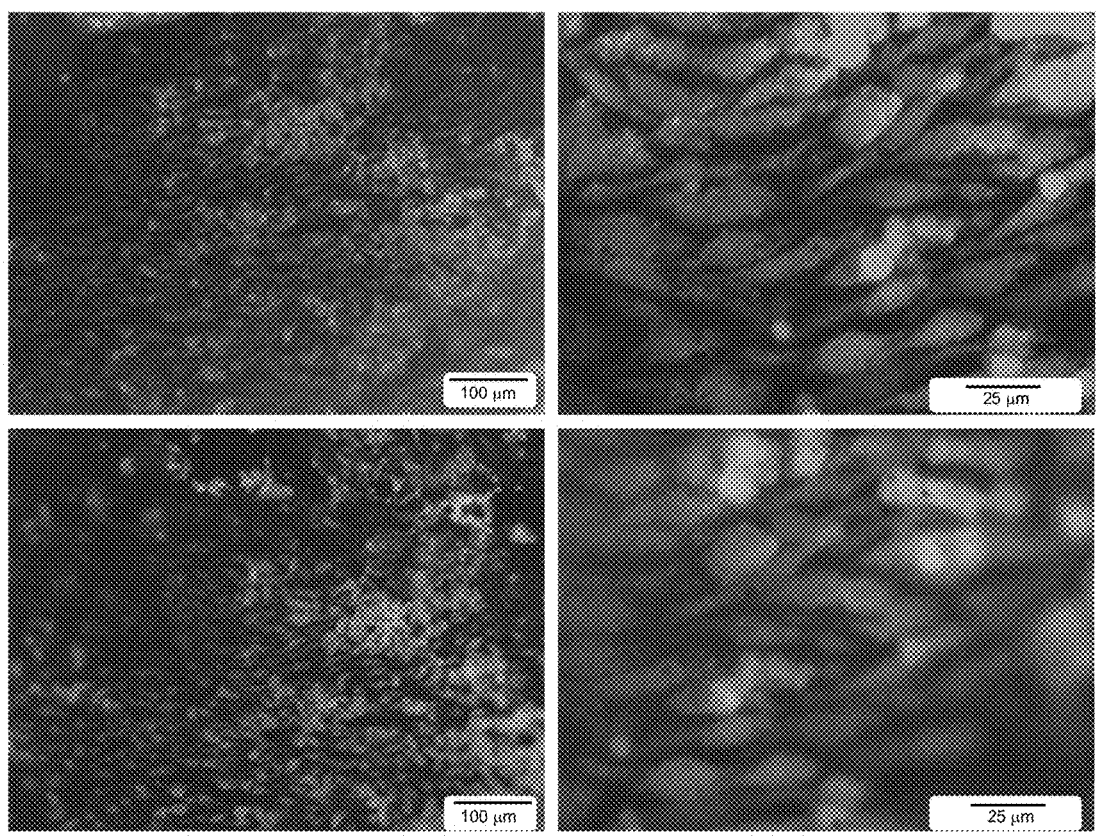

FIG. 33 illustrates Calcein AM and Calcein AM and DAPI stained images of cardiomyocytes on selected regions of LCE under cyclic heating. LCEs was stimulated through 12 W heating power and 6.5 s pulse duration, producing approximately 5% uniaxial strains during cell culture. The primary strain direction is horizontal in the images above. Images are at 10× (left) and 40× (right) magnification. The cells were stained using Calcein AM (Biotium) while the nuclei was stained with VectaShield DAPI-containing mounting medium (Vector Lab). The images were then observed and imaged using a fluorescent microscope.

Figure 34:
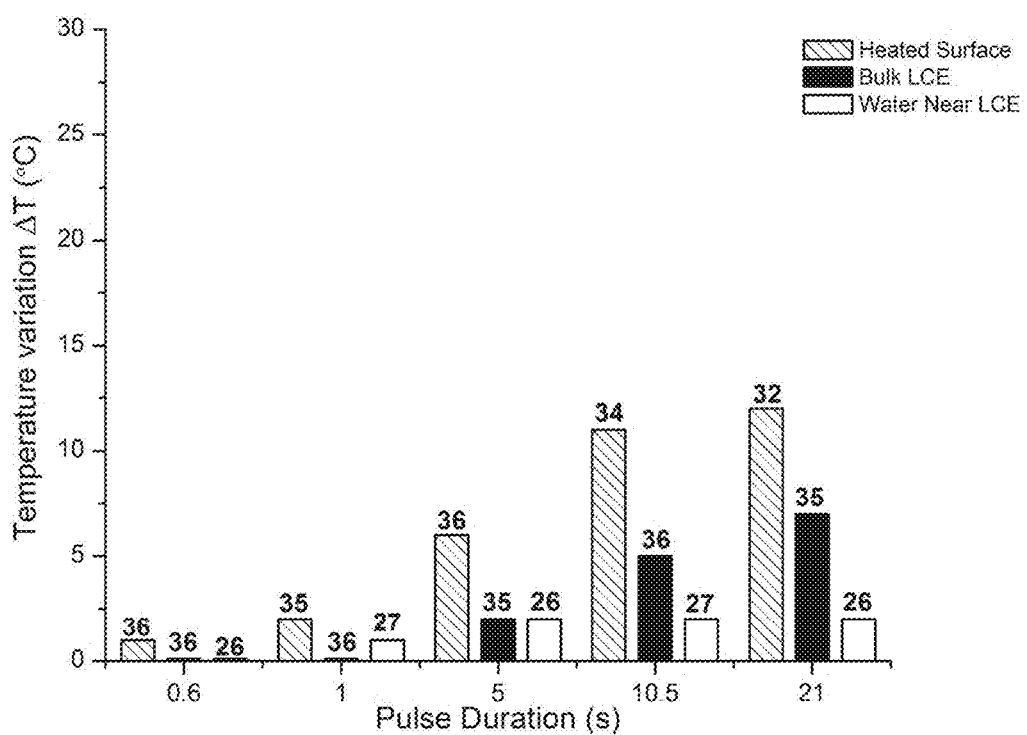

FIG. 34 illustrates temperature variation near the surface of the resistive heater, in the bulk LCE, and near the LCE surface under cyclic heating for 5 W heating power. The values above each bar indicate the average temperature for each case. All samples were allowed to equilibrate for at least 10 min under cyclic heating. The ambient temperature was approximately 25° C.

Figure 35:
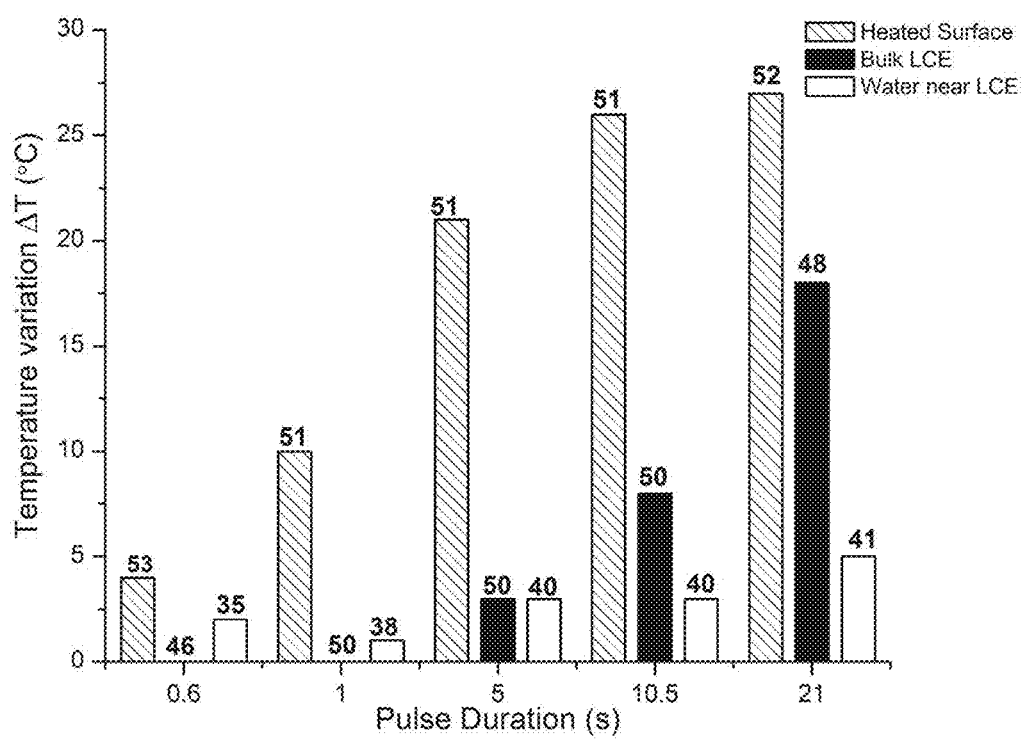

FIG. 35 illustrates temperature variation near the surface of the resistive heater, in the bulk LCE, and near the LCE surface under cyclic heating for 20 W heating power. The values above each bar indicate the average temperature for each case. All samples were allowed to equilibrate for at least 10 min under cyclic heating. The ambient temperature was approximately 25° C.

Figure 36:
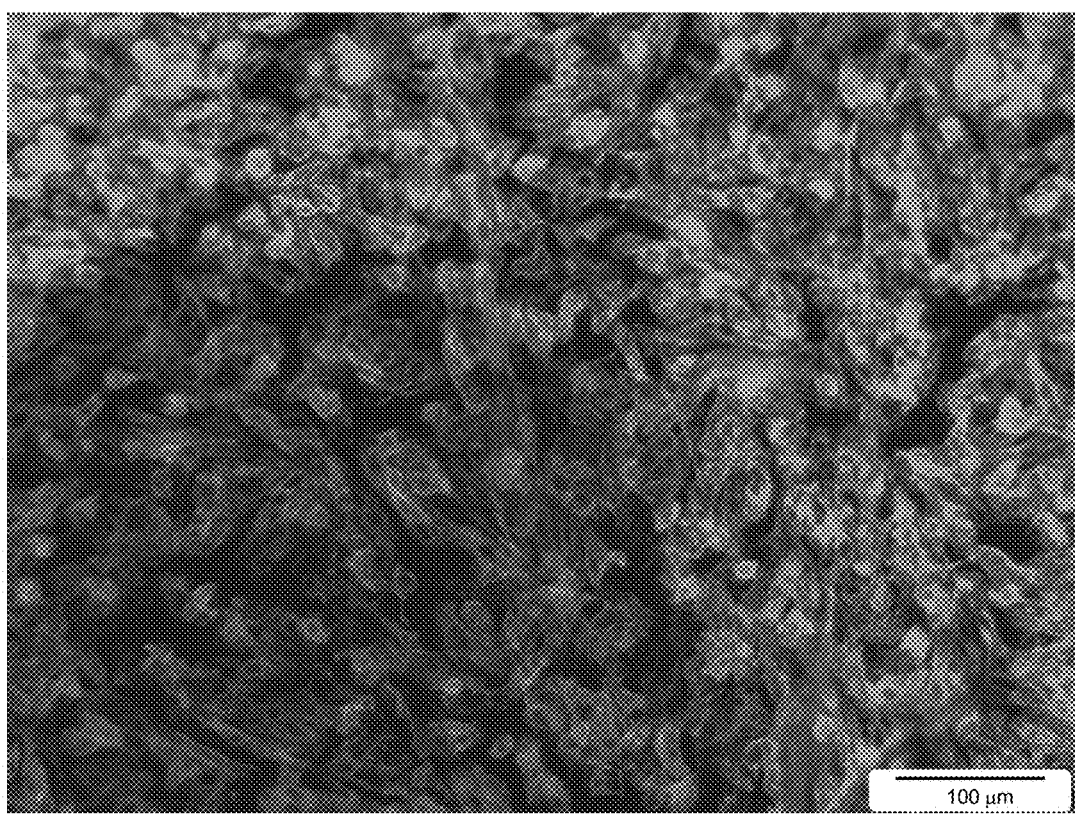

FIG. 36 illustrates phalloidin (Alexa Fluor 488, Life Technologies) stained images of cardiomyocytes on LCEs under cyclic heating (12 W, 6.5 s pulse duration).

While the present disclosure is susceptible to various modifications and alternative forms, specific example embodiments have been shown in figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure may be embodied in other specific forms without departing from its essential characteristics. The described embodiments are to be considered in all respects only as illustrative and not as restrictive.

The present disclosure generally relates to responsive materials such as liquid crystal elastomers and their use in culturing cells and cell sheets. Cells have the unique ability to sense their environmental physical cues such as mechanical properties and topographical features of the substrates. These physical cues are shown to affect cell alignment, adhesion and traction forces. Passive cell culture substrates, however, are limited in their ability to tune or program substrate topography or mechanical properties during cell culture.

For clinically relevant cell sheet function, mechanosensitive cells, such as cardiac myocytes must be able to generate force sufficient to significantly aid heart contraction, and they should conduct depolarization waves at speeds comparable to the native myocyardium to avoid the possibility of generating arrhythmias. Studies have shown that random monolayer distributions of cardiomyocytes results in force generation and conduction speeds of the depolarization wave that are much lower than in native tissues. However, the systems and methods of the present disclosure provide aligned mechanosensitive cells and allow for rhythmic mechanical conditioning resulting in much higher forces and wave conduction speeds.

The present disclosure provides responsive liquid crystal elastomers that are biocompatible, shape-responsive substrates that provide a scalable technique for aligning cell sheets. The present disclosure also provides systems and methods that use responsive liquid crystal elastomers. Such systems and methods may be used to grow cells and to form aligned cell sheets. The responsive liquid crystal elastomers of the present disclosure provide a dynamic surface pattern providing reversible topography changes. Such dynamic surfaces offer improved cell alignment in cell sheets as compared to those grown on static surfaces or on mechanically flexed substrates. Additionally, the methods and substrates of the present disclosure provide an affordable and scalable method to grow aligned cell sheets. These cell sheets can aid in the treatment of patients in need of cell sheets, for example, patients suffering from heart disease.

In certain embodiments, the present disclosure provides a method comprising culturing a plurality of cells on a liquid crystal elastomer substrate (LCES) comprising a first shape characteristic or first topography. Following an initial period of stimulus-free culture to permit the cells to sufficiently adhere to the surface of the LCES, a stimulus is applied to the LCES of a sufficient intensity to cause the liquid crystal elastomer substrate to change from the first shape characteristic to a second shape characteristic. The stimulus is removed and the LCES is then allowed to return to the first shape characteristic such that stimulus induced shape characteristic change is reversible. These steps will typically be performed while maintaining the LCES and cells under culture conditions in appropriate culture media.

As used herein, the term "shape characteristic" includes the surface topography of the liquid crystal elastomer substrates such as, for example, a flat or wrinkled, size of the LCES resulting from contraction and elongation, substrate modulus including the rigidity or stiffness of the substrate, and other structural changes that may benefit cell growth, differentiation, or alignment.

In general, the cell may be any type of cell that may benefit from physical cues the promote growth, alignment, strength, and maturity. In one embodiment, the cells are mechanosensitive cells such as cardiomyocytes. In other embodiments the cell may be a self-replicating progenitor cell; for example, a self-replicating cardiac progenitor cell. Such self-replicating cardiac progenitor cells may be isolated from, for example, heart tissues routinely excised during surgeries to correct congenital heart defects. The cells may be cultured to form cell sheets.

The cells may be seeded on the LCES at a variety of densities based on the size of the substrate and the type of cell being used. For example, cardiomyocytes can be seeded at a density of 100,000 to 1,000,000 cells per square cm. The ability of the cells to adhere to the LCES is based on a surface layer comprising one or more of a variety of materials that promote cell adhesion such as, for example, gold, collagen, fibronectin, and polystyrene. In certain embodiments, the cells are seeded on the LCES and allowed to culture for 24 hours before applying the first stimulus. However, this time period may need to be extended or in some instances, can be shortened based on the type of cell being utilized.

After the cells are properly seeded on the LCES and an appropriate initial culture period has occurred, a stimulus is applied to the liquid crystal elastomer substrate sufficient to cause the liquid crystal elastomer substrate to change from the first shape characteristic to a second shape characteristic. The stimulus may include light, mechanical strain, magnetic or electric field induced alignment, or compression. Additionally, in certain embodiments, a thermal stimulus is utilized to induce a shape characteristic change in the LCES. For example, as depicted in FIG. 27, the LCES can be placed on a resistive heater and a power source provides a heating power thereto from about 5 watts to about 20 watts for a pulse duration of about 0.1 seconds to about 1000 seconds thereby leading to a change in a first shape characteristic to a second shape characteristic in the LCES. In other embodiments, the pulse duration is from about 0.5 seconds to about 20 seconds, and further may be from about 1 second to about 5 seconds. In this example, the heating power can be about 12 watts. These stimuli are generally sufficient to provide a provide a reversible strain from about 0.1% to about 50% on the liquid crystal elastomer substrate, and in some instances, provide a reversible strain of about 5%.

In other embodiments, the LCES can be manufactured to include a conductive material, such as carbon nanoparticles or carbon black nanoparticles, as will be discussed in further detail herein below, such that an electrical stimulus will be applied directly to the LCES to induce the shape characteristic change.

In these and other embodiments, the stimulus is repeated one or more times and in some instances, can be constantly repeated for one or more days. Generally, the time required to allow the liquid crystal elastomer substrate to reverse from the second shape characteristic back to the first shape characteristic will coincide with the pulse duration of the stimulus. For example, a stimulus pulse duration of 2 seconds to induce the change from the first shape characteristic to the second shape characteristic will be followed by a period of 2 seconds to allow the LCES to revert back to the first shape characteristic before applying subsequent stimuli at the same or different pulse durations. As explained herein, the pulse durations, pulse frequency, time on an off, and number of cycles will be dependent on the type of material, its density, the thickness of the material, the environment around the LCE (e.g. air or water) and the desired stimuli to apply to the cells.

A cell culture substrate is also provided. In certain embodiments, the cells are cultured on a shape-responsive substrate that is generally reversibly, shape-response to various stimuli and comprises a bilayer formed from, for example, one or more shape-responsive layers and a cell adhesion layer.

In one embodiment, the shape-responsive layer comprises a liquid crystal elastomer. LCEs generally comprise rubbery polymeric networks with long-range orientational and/or positional order and include networks of flexible polymer chains with liquid crystalline order. LCEs exhibit 'soft elasticity' that is exemplified by large-strain deformations with little resistance. In addition, network chains in LCEs are often locally anisotropic and assume an ellipsoidal conformation, in contrast to the spherical random coil conformation of conventional isotropic rubbers. The individual molecules that comprise a liquid crystal are commonly referred to as mesogens. These molecules tend to be 'rod like' or anisotropic structures, with one axis appreciably longer than the other axis. However, LC phases have been prepared using mesogen of a wide variety of shapes, including ring structures, banana, hockey stick, and T shaped molecules.

In general, LCEs can change shape reversibly in response to a stimulus, such as, for example, light, temperature, and electric fields. Shape-changes in monodomain LCEs, which have a uniformly aligned liquid crystal (LC) director, can range from 10% to 400% of the initial LCE size.

In some embodiments, the LCE is a polydomain liquid crystal elastomer. In some embodiments, the LCE includes a nematic director and a mesogen (liquid crystal molecule) associated with a polymer. In some embodiments, the mesogen content of the LCE ranges from about 20% molar content to about 90% molar content of the liquid crystal elastomer. In some embodiments, the mesogen is generally a molecule that produces a liquid crystal phase at room temperature and may include at least one of aromatic rings, aliphatic rings, poly aromatic rings, poly aliphatic rings, phenyls, biphenyls, cyanobiphenyls, benzenes, and combinations thereof. In some embodiments, the mesogen is functionalized with one or more functional groups, such as alkenes, alkanes, alkynes, carboxyl groups, esters, halogens, and combinations thereof. In certain embodiments, the mesogen is 4-methoxyphenyl 4-(3-butenyloxy) benzoate.

In some embodiments, mesogens in LCEs are cross-linked polymers. In some embodiments, the polymer includes at least one of polysiloxanes, poly(methyl) siloxanes (PMS), poly(dimethyl) siloxanes (PDMS), polymethylhydrosiloxane (PMHS), poly(methyl methacrylate), polyethylene, polypropylene, poly(butylacrylate) network chains and combinations thereof.

The polymers may be associated with mesogens in various arrangements. For instance, in some embodiments, the mesogens may be cross-linked to polymers. The crosslinker can be any reactive molecule that produces a physically or chemically crosslinked, elastomeric network. For example, a di(methacrylate) crosslinker is used or a diacrylate crosslinker. The crosslinker concentration can be varied to increase or decrease the elastomer modulus, at higher or lower crosslinker contents, respectively. Other catalysts or methods can be used to crosslink the network, including thermal annealing or platinum catalysts that are more or less reactive. The solvent content can also be varied during synthesis.

In some embodiments, a plurality of mesogens may be covalently coupled to a single polymer chain. In some embodiments, a plurality of mesogens may be covalently coupled to multiple polymer chains. In some embodiments, the mesogens and polymers may be intertwined within a matrix. LCEs may be made using methods known in the art. For example, LCEs may be made using a two-step cross-linking method as described in Küpfer, J. & Finkelmann, H., Nematic liquid single crystal elastomers. *Macromol Chem Rapid Commun,* 12 (12), 717 (1991).

In yet another embodiment, conductive material can be added to the shape-responsive layer. The conductive filler can provide the LCE nanocomposite with an electrical, magnetic, or light-induced response, as examples. For example, the LCE may comprise one or more wires. Alternatively or in addition to, carbon nanotubes, carbon black nanoparticles, or conductive gold nanoparticles can be used. The response of the resulting polymer nanocomposite should be reversible and the material should be stable to operation for up to several weeks.

In one particular example, carbon black nanoparticles can be employed into the shape-responsive layer of the present cell culture substrate. In some instances, the carbon black nanoparticle can be added to the mesogen and polymer during the cross-linking step thereby causing the carbon black nanoparticle to be uniformly dispersed in the shape-responsive layer. Alternatively, or in addition, the carbon black nanoparticles can be added to the shape-responsive layer by immersion in toluene comprising a concentration of carbon black nanoparticles. This alternative or additional step results in an increased concentration of carbon black nanoparticles at the edges of the shape-responsive layer.

The cell culture substrate also includes a cell adhesion layer. The cell adhesion layer may be formed from any polymer suitable for use with cells. Examples of suitable polymer include, but are not limited to, poly(styrene), and other biocompatible polymers known in the art. The polymer layer may be applied to the LCE layer to form a bi-layer. For example, the polymer layer may be transferred onto the surface of the LCE. In certain embodiments, polymer films can be used to coat the top surface of the shape-responsive layer. For example, an LCE layer is coated through transfer of a thin polystyrene (PS) film. A polystyrene film is prepared by spin-casting a solution of polystyrene in toluene onto a UV-ozone cleaned silicon substrate. The LCE is then placed face-down on top of the substrate, and the entire substrate and LCE is immersed in water for 10 hours. The LCE is then peeled off and dried under vacuum. The PS film thickness can be varied, and other polymers can be used as top-surface coatings. In addition, the cell adhesion surface may be further coated with a metal, protein or other materials that enhance cell attachment. The inclusion of carbon black nanoparticles in the shape-responsive layer may provide cell culture substrates possessing an electrical resistivity of from about 0.1 Ω·m to about 10.0 Ω·m, an elastic modulus of from about 3 kN to about 9 kN, and a thermomechanical strain from about 1% to about 27%.

In another embodiment, the cell adhesion layer comprises gold and collagen. For example, the shape-responsive layer, here LCE, is exposed to Oxygen-plasma for 20 seconds (Model 2010 Fischione Instruments Plasma Cleaner) and then immediately coated with a 30 nm gold layer using a Denton Desk V sputter system. Next, the samples are treated with UV-ozone for 10 minutes (Jelight, Model 42 UVO cleaner) and a solution of collagen type 1 (3.4-3.6 mg/ml) from Rat Tail (Corning, product number 354236) with a concentration of 50 ug/ml in 0.02N acetic acid is applied to the gold-coated LCE surface. A drop of the collagen (using a 20-200 ul pipette tip) solution is placed on the LCE to cover just the surface. This is left for 2 hours at room temperature or overnight at 4 degrees centigrade. Afterwards the LCE is preconditioned in the incubator at 37 degrees and 5% CO2 for a minimum of 1 hr before cell seeding.

As noted above, the responsive liquid crystal elastomer provides a dynamic surface on which cells may be cultured. Accordingly, the responsive liquid crystal elastomer provides a surface that at least partially changes topography in response to a stimulus. Both the wavelength and amplitude of topography change can be tuned either by polymer film thickness or magnitude of the stimulus applied. The particular topography may depend on the particular stimulus, LCE, and thickness of the layers. The topography may change by providing a surface that is flat, aligned wrinkled, and random wrinkled morphologies. The change in topography may be stimulated by, for example, light (e.g., UV light), temperature changes, and electric fields, or combinations thereof. In certain embodiments, the stimulus is an electric field that provides dynamic strain similar to that in a native heart environment.

EXAMPLES

Formation and Preparation of Liquid Crystal Elastomer (LCE) Bi-Layers

Uniformly aligned, side-chain nematic liquid crystal elastomers LCEs were prepared by the two-step crosslinking as described in as described in Küpfer, J. & Finkelmann, H., *Macromol Chem Rapid Commun,* 12 (12), 717 (1991). Briefly, liquid crystal (mesogen) monomer, crosslinker, and PMHS as depicted in FIG. 1 are dissolved in toluene along with platinum catalyst dichloro(1,5-cyclooctadiene)platinum(II). First, partial crosslinking is achieved by heating the reaction mixture for several hours. In a second step, the partially crosslinked elastomer is stretched by applying a load and then annealed at room temperature for several days. This results in uniform orientation of director along the stretching direction. For this study, LCEs with 10% crosslinking density were used.

The hydrosilylation reaction of a vinyl terminated mesogen and a diacrylate crosslinker (10 mol %) with PMHS results in a lightly crosslinked liquid crystal (LC) network with uniform alignment due to strain imposed during crosslinking as shown in FIG. 1. Alignment is confirmed by polarized optical microscopy and by the reversible shape-change of the LCE with temperature as shown in FIG. 2.

Monodomain LCEs spontaneously change shape as a function of temperature due to the temperature dependent order parameter of the LC mesogens, and the shape change is fully reversible on both heating and cooling the sample.

Next, nanoscale polystyrene ("PS") films were prepared by spin-casting a 0.25-3 wt % PS solution (Mw=271 kg/mol, polydispersity=1.02, Polymer Standards Service-USA Inc) onto a silicon substrate cleaned by UV-ozone treatment. To transfer the PS film to the LCE substrate, the LCE was gently placed on top of the PS film, immersed in water at a fixed temperature for 10 hours, and then peeled off and dried under vacuum. This method can be used to prepare LCE-PS bilayers with different PS film thicknesses and at different preparation temperatures.

Surface Wrinkling in LCE Bi-Layers Using Thermal Stimulus

To test whether surface wrinkling could be induced with temperature changes in LCE bilayers, we prepared two PS-LCE bilayer samples, both with a 30 nm PS film and a 0.36 mm-thick LCE. The first sample was prepared by film transfer at 30° C. and the second at 60° C. Surface wrinkling in both of these samples was monitored using optical microscopy equipped with a home-built heat stage. As shown in FIG. 3, the sample prepared at 30° C. is uniform at room temperature but exhibits surface wrinkling when the temperature is increased to 40° C. As the temperature increases, the LC order parameter decreases and the LCE spontaneously deforms, with contraction along the director (and dilation in the perpendicular directions) resulting in surface wrinkles above a critical strain (approximately 5%, achieved at 40° C.). Conversely, for the sample prepared at 60° C., surface wrinkles oriented parallel to the nematic director appear upon cooling the sample. The LC order parameter increases as the temperature is decreased, resulting in a spontaneous elongational strain in the direction parallel to the global nematic director (and compressive stress normal to the director). For both cases, the wavelength of the surface wrinkles is independent of temperature above the critical strain.

LCE bilayers uniquely enable the reversible reorientation of wrinkles with temperature in a single sample. As shown in FIG. 4a, an LCE-PS bilayer prepared at 50° C. is uniform at 50° C. but exhibits surface wrinkles parallel to the nematic director if the sample is cooled below the preparation temperature. Conversely, if the sample is heated above the preparation temperature (to 60° C.) surface wrinkles appears oriented perpendicular to the nematic director. This response is fully reversible with temperature.

While relatively small temperature changes (20-30° C.) below the glass-transition temperature Tg of the PS film give reversible surface wrinkling patterns, larger temperature changes over a range that exceeds the Tg of the PS film can also be used to erase and re-orient surface wrinkles. To demonstrate this, a 50 nm PS thin film was transferred onto the LCE substrate at 30° C. and subsequently heated to the Tg (~105° C.) of the PS film (FIG. 4b). Surface wrinkles oriented perpendicular to the nematic director appear at temperatures below the Tg, but upon annealing the sample near the Tg of PS, surface wrinkles are 'erased' due to viscoelastic flow of the PS film. The surface becomes uniform after annealing for approximately 30 minutes, and on subsequent cooling surface wrinkles reappear oriented parallel to the nematic director. Similar phenomena have been reported in previous studies. Since the formation of cracks in the top PS film makes the LCE based wrinkling instability reversible only for small strain values (<5%), one way of overcoming this drawback is by considering that the modulus of the top polymer film and the nematic-to-isotropic transition temperature of the LCE can be tuned to target a desired temperature range.

Surface wrinkles in bilayer samples are a type of Euler buckling instability where the stiff, thin film (PS in the present study) is in contact with a softer and thicker substrate; compressive stress leads to more favorable short wavelength displacements in-comparison to simple bowing. The wavelength of the surface wrinkles can be quantitatively described using the Euler-Bernoulli beam-bending equation with the assumption that the polymer film is significantly thinner than the LCE substrate and has a substantially greater modulus.

$$\lambda = 2\pi h \left( \frac{\bar{E}_f}{3\bar{E}_s} \right)^{\frac{1}{3}} \quad (1)$$

As shown in Eq. 1, the wavelength λ of the surface wrinkling patterns depends on the film thickness h, the film plane-strain modulus $\bar{E}_f = E_f/(1-v_f^2)$, where $E_f$ and $v_f$ are the Young's modulus and Poisson's ratio for the film, respectively, and the substrate plane-strain modulus $\bar{E}_s = E_s/(1-v_s^2)$, where $E_s$ and $v_s$ are the Young's modulus and Poisson's ratio of substrate, respectively.

The relationship in Equation 1 forms the basis of the technique known as strain-induced elastic buckling instability for mechanical measurements (SIEBIMM) and enables calculation of the thin film modulus via measurement of the wavelength of surface wrinkles and the modulus of the deformable substrate. This method has been used to characterize the properties of a variety of materials, including metal films, polymer brushes, polymer nanocomposites, carbon nanotubes, among others. SIEBIMM was applied to measure the modulus of the nanoscale PS films and to test whether the relationship between the surface wrinkle wavelength and film modulus follows Equation 1.

The elastic modulus of the LCE substrate was measured with a dynamic mechanical analyzer (DMA-Q800) and found to be 0.24 MPa. Using the same LCE sample, we tested PS film thicknesses ranging in thickness from 30 nm up to 400 nm as shown in FIGS. 5a and 5b. Samples were prepared at room temperature and heated to 60° C. to create surface wrinkles, and the wavelength of surface wrinkles was measured with an optical microscope. As shown in FIGS. 5a and 5b, the wavelength increases linearly with PS film thickness and varies from 2 μm up to 40 μm over this PS film thickness range. By applying Equation 1, we find that for film thicknesses greater than 100 nm, the measured modulus is in good quantitative agreement with the bulk PS modulus of 3.5 GPa. At film thicknesses below 50 nm, we observe a drop in the film modulus, i what has been previously observed in SIEBIMM measurements. These data indicate that LCEs are reliable substrates for measurement of polymer moduli via SIEBIMM without the need for clamping the sample.

Above a critical thickness of the PS film (for 0.36 mm thick LCE), surface wrinkling is no longer favored. Instead, due to the elongational anisotropy of the PS and LCE films, PS-LCE bilayers exhibit reversible curling. This was observed for a bilayer sample prepared at room temperature with a 986 nm-thick PS film and 0.36 mm-thick LCE. While initially flat at room temperature, the bilayer reversibly curls over a temperature range of 50-80° C., near the nematic-to-isotropic transition temperature ($T_{NI}$) of the LCE (see FIGS. 6a and 6b a). The LCE curling phenomenon is found to be very reversible as illustrated in FIG. 6b, with only slight hysteresis is observed after subjecting the sample to several heating and cooling cycles. This response analogous to the bending and twisting of elastomers by non-homogeneous swelling and the reversible curling in metallic bilayer strips, where the curvature of bilayer is proportional to the difference in elongation of the two layers. An advantage of the PS-LCE bilayer system is the large strains that are achieved over a temperature range of approximately 10° C. The performance is comparable to those demonstrated in dielectric elastomer actuators (strains up to 300% have been reported by applying an electric field of 420 MVm−1) but can be achieved with temperature changes instead of external voltages.

Surface Wrinkling in LCE Bi-Layers Using Electrical Stimulus

One way to make LCEs electrically responsive is by incorporating ferroelectric mesogens into rubbery matrix. Under the application of electric field, these mesogens change their alignment leading to electromechanical effect in LCEs. However, requirement of strong electric field and the resulting small amplitude mechanical response limits their applications. Earlier studies have shown that resistive heating mechanism can also be used to induce shape change in LCE with electric field and can offer fast response times. And the only requirement for that is conductive LCE. In general, this is accomplished by embedding wires or conducting nanoparticles within the host LCE matrix. These filler particles generate heat on application of electric field, thereby causing mesogens to undergo phase transition and contract. However, addition of wires or nanoparticles inside LCE matrix increases the modulus of resulting composite thus restricting the final shape change.

Synthesis of LCE Using Immersion-Dispersion Approaches

LCEs were synthesized using three different approaches (i) immersion (LCE-I), (ii) dispersion (LCE-D) and (iii) a combination of immersion and dispersion (LCE-DI)

In an immersion approach, monodomain LCEs were swollen in a solution containing carbon nanoparticles for a period of 1 day. Choice of solvent is based on the LCE solubility. Solvents like methanol and hexanes are poor solvents for LCE network, resulting in no or very less penetration of nanoparticles within the network. On the other hand, dichloromethane is an extremely good solvent and it basically tears apart the LCE network (FIG. 3). Toluene was found to be an appropriate solvent. In toluene, LCE expands reasonably (~400%) causing nanoparticles to penetrate few micrometers inside the rubbery network and thereby decreasing the resistivity of the resulting composite. Similar results were observed in previous studies as well. In addition, nanoparticles concentration in solution has a significant effect on LCE resistivity. But after critical concentration of 7 g/l there is no major change in the effective LCE resistivity with increasing the nanoparticles concentration in the solution. Afterwards, air drying the sample leaves behind a thin micrometer thick conductive layer of nanoparticles on the LCE surface (FIG. 13). This thin conductive layer facilitates resistive heating to induce electromechanical response in LCE-I. (Figure to be included in the future) shows the optical microscopy of LCE-I prepared using 7 g/l nanoparticles concentration solution.

For a dispersion approach, two-step method was adopted for the preparation of carbon nanoparticles enriched monodomain LCEs (FIG. 14). Briefly, nanoparticles were added to the liquid crystal monomer mixture along with the other starting materials prior to the first crosslinking step. Common difficulty with this approach is nanoparticles tends to precipitate from the reaction mixture and form a layer on LCE surface. To avoid this issue, we performed the first crosslinking in a mold along with a slow rocking motion. This creates a slight agitation to prevent nanoparticles from falling out of the solution. FIG. 14 shows the optical microscopy images of LCE-D having different weight percentage of carbon black particles.

Immersion+dispersion approach: In this modified approach, both immersion and dispersion approaches are combined to achieve LCE with the lowest effective resistivity (FIG. 15). In this approach, 4-(3-Butenyloxy)benzoic Acid 4-methoxyphenyl ester (166.2 mg, 0.557 mmol), 1,4-di(10-undecenyloxy)benzene (12.8 mg, 0.0310 mmol), polymethylhydrosiloxane (40 mg, Mw=2300 g/mol), and conductive carbon black nanoparticles (4.38 mg, 2 wt % relative to total liquid crystal, crosslinker, and polymethylhydrosiloxane content) are dissolved in 0.6 mL toluene along with 30 microliters of a 1 wt % solution of platinum catalyst dichloro(1,5-cyclooctadiene)platinum(II) in chloroform. The reaction mixture is added to a rectangular Teflon mold (3 cm×2 cm×1 cm) and heated to 60° C. for 1 hour with gentle agitation. Next, the partially crosslinked elastomer is carefully removed from the Teflon hold and hung vertically under load. The LCE is hung vertically and 2.3 g of weight is attached to the opposite side of the LCE to apply a load. The LCE is hung under load at room temperature for at least 7 days during which the crosslinking reaction is complete. After completion of the crosslinking reaction, the LCE is immersed in toluene and dried in air to remove unreacted material. After complete drying of the material, the LCE is immersed in toluene with 10 g/L concentration of carbon black nanoparticles for surface infiltration of additional carbon black through solvent swelling. FIG. 15 shows the optical microscopy of LCE-DI having different weight percentage of carbon black particles.

A comparison of LCE nanocomposites prepared using immersion+dispersion approach described above with LCE nanocomposites prepared by adding carbon black nanoparticles only during crosslinking is provided below in Tables 1 and 2.

TABLE 1

Properties of LCE nanocomposites with varying amounts of carbon black added during crosslinking (1$^{st}$ step) and then by swelling in chloroform solution (2$^{nd}$ step).

| Sample | NP Conc. in LCE$^a$ (wt %) | NP Conc. in chloroform$^b$ (g/L) | Electrical Resistivity ($\Omega \cdot m$)$^c$ | Elastic Modulus (kN) | Thermo-mechanical strain (%)$^d$ | Stable electro-mechanical response? |
|---|---|---|---|---|---|---|
| LCE90 | 0 | 0 | ∞ | 1.1 | 35.0 | N/A$^e$ |
| LCE90-I | 0 | 10 | 38.5 | 2.1 | 35.0 | No |
| DI1% | 1 | 10 | 25.1 | 2.9 | 27.7 | No |
| DI2% | 2 | 10 | 7.5 | 3.5 | 22.5 | Yes |
| DI4% | 4 | 10 | 4.1 | 4.9 | 17.5 | Yes |
| DI6% | 6 | 10 | 3.5 | 5.1 | 16.3 | Yes |
| DI8% | 8 | 10 | 2.05 | 5.5 | N/A | Yes |
| DI10% | 10 | 10 | 1.6 | 6.1 | 8.3 | Yes |
| DI15% | 15 | 10 | 0.68 | 7.2 | 5.2 | Yes |
| DI20% | 20 | 10 | 0.22 | 8.1 | 2.2 | Yes |

$^a$wt % of carbon black nanoparticles added during LCE crosslinking and synthesis. wt % is relative to total liquid crystal mesogen, crosslinker and polysiloxane content
$^b$After crosslinking, the LCE nanocomposite can be immersed in a solution of chloroform to increase the nanoparticle content. The value shown in the concentration of carbon black nanoparticle in the chloroform solution
$^c$where ∞ is shown, the material is insulating and has no measurable electrical conductivity
$^d$Thermo-mechanical strain is measured by measuring the spontaneous sample contraction along the primary length when heating from room temperature to above the $T_{NI}$, roughly 80° C.
$^e$pure LCEs do not exhibit any measurable electro-mechanical response The table above shows that adding nanoparticles in two steps produces an LCE nanocompostie that is electro-mechanically shape responsive. For example, sample DI4% exhibits strains up to 17% and has an electrical resistivity of 4.1 $\Omega \cdot m$. At lower nanoparticle contents added in the 1st step, the conductivity decreases and the electro-mechanical response is unstable. For no nanoparticle added, the LCE is unresponsive. At higher nanoparticle contents added before crosslinking (1st step), the LCE nanocomposite becomes very stiff and the electro-mechanical response is dampened. For example, DI 20% has an elastic modulus of 8.1 kN and a maximum strain of only 2.2%.

In other embodiments of the material, carbon black is only added in the 1st step, during the crosslinking reaction. As shown in Table 2 below, when carbon black nanoparticles are added only during LCE synthesis (1st step), the final material is not electrically conductive until relatively large amounts of conductive carbon black are added. At these higher carbon black contents, the mechanical response of the material is poor.

TABLE 2

Properties of LCE nanocomposites with conductive carbon black added only during crosslinking (1st step) without swelling in chloroform

| Sample | NP Conc. in LCE[a] wt % | Electrical Resistivity ($\Omega \cdot m$)[b] | Thermo-mechanical strain[c] (%) | Electro-mechanical strain[d] (%) | Stable electro-mechanical response?[e] |
|---|---|---|---|---|---|
| D1%  | 1  | ∞    | 27.7 | 0   | N/A |
| D2%  | 2  | ∞    | 22.5 | 0   | N/A |
| D4%  | 4  | ∞    | 17.5 | 0   | N/A |
| D6%  | 6  | ∞    | 16.3 | 0   | N/A |
| D10% | 10 | ∞    | 8.3  | 0   | N/A |
| D15% | 15 | 1.05 | 5.2  | 4.1 | Yes |
| D20% | 20 | 0.25 | 2.2  | 1.9 | Yes |

[a]wt % of carbon black nanoparticles added during LCE crosslinking and synthesis. wt % is relative to total liquid crystal mesogen and polysiloxane content.
[b]where ∞ is shown, the material is insulating and has no measurable electrical conductivity.
[c]Thermo-mechanical strain is measured by measuring the spontaneous sample contraction along the primary length when heating from room temperature to above the $T_{NI}$, roughly 80° C.
[d]electro-mechanical strain measured by applying a 20 V, 60 Hz AC electrical signal to the sample.
[e]Where N/A is indicated, no measurable electro-mechanical response was observed.

Comparison to prior work demonstrates the advantages of the two-step method for preparing liquid crystal nanocomposites. If the carbon black is only introduced by solvent swelling (2nd step) the resulting material exhibits an unstable electro-mechanical response, as reported by Chambers, M.; Finkelmann, H.; Remškar, M.; Sánchez-Ferrer, A.; Zalar, B.; Žumer, S. J. Mater. Chem. 2009, 19, 1524. Similarly, when the carbon black nanoparticle is only added during the LCE cross-linking (1st step), the results of Table 2 demonstrates that the properties are not as advantageous.

LCE with Nanoparticles

Since for carbon black nanoparticles (nps) particle-particle interaction is very high, they have natural tendency to aggregate to reduce surface energy. Since uniform dispersion of nps has a significant effect on the properties of the final LCE-composites, we verified uniform dispersion of nps within LCE matrix both by the optical microscopy. For LCE-I there is a 3 μm thin layer of nps on the LCE surface. But LCE composites prepared by dispersion and combination of dispersion+immersion approach appears completely black under optical microscopy. These results show that nps are distributed throughout the LCE matrix.

DSC

Understanding the phase transition properties of LCE composites is important to understand effect of nps on liquid crystalline properties. Based on differential scanning calorimetry measurements (FIG. 16), thermal phase transition behavior of LCE composites is similar to that of the neat LCE with a little shift of about few degrees in nematic-isotropic transition temperatures. We found that for LCE composites with low nps concentration (≤2 wt %) shift in $T_{NI}$ is few degrees on the lower side compared to neat LCE. But for concentration higher than 2 wt %, $T_{NI}$ tends to be few degrees higher than that for neat LCE.

Mechanical Properties

Main aim behind incorporating nanoparticles within LCE matrix is to enhance electric properties/quick response times of the overall composite without altering its liquid crystalline and thermo-mechanical properties. FIG. 17 shows the stress-strain behavior of different LCE composites used in this study. As expected, addition of nanoparticles increases the elastic nature of the composite, which could aid in its quick response times. LCE-I and LCE have relatively similar modulus as expected, since in LCE-I nps form a very thin coating only on the LCE surface. LCE-D2% and LCE-D4% have slightly higher modulus. But in case of LCE-D10%, elastomer composite is extremely stiff with respect to the neat LCE. Both LCE-DI2% and LCE-DI4% have mechanical properties similar to LCE-D2% and LCE-D4% respectively.

Thermo-Mechanical Response

Neat, monodomain LCEs spontaneously change shape as a function of temperature due to the temperature dependent order parameter of the LC mesogens, and the shape change is fully reversible on both heating and cooling the sample. FIG. 18 shows the thermal response of LCE and LCE composites along the nematic director as a function of temperature. LCE samples were mounted between the tension clamps on DMA-Q800. System temperature was then increased at 5° C./min and data points were collected at an interval of 0.1 s. Neat monodomain LCEs showed the maximum expansion of about 35%. Adding nanoparticles to the LCEs, should exhibit either similar or weakened thermal actuation. Conductive LCEs prepared by the immersion approach (LCE-I) exhibits similar response to the neat LCEs. While LCEs prepared by the dispersion approach show weakened response. LCEs with 2% and 4% CB nps show 22% and 17% strain along the director. LCE composites prepared by combination of dispersion and immersion approaches behaves similarly as their corresponding composites prepared by just dispersion approach with similar nps concentration.

Another advantage of DI approach is the increase in thermal conductivity of the overall composite. Due to the low thermal conductivity of LCEs, heat transfer across the LCE is relatively slow which affects its response time. But by uniformly dispersing carbon black nanoparticles throughout the polymeric LCE matrix, thermal conductivity of the overall composite increases which generates faster response times and overall better control over the actuation. This could be seen in FIG. 18, where slope of the curve becomes more steep with increasing CB nps concentration.

WAXS Measurements

The reason for the weakened response after addition of nps within LCE matrix could be due to many reasons like poor alignment (low order parameter) of LC polymer chains, increase in stiffness of the final composite or alteration of liquid crystalline properties. For better understanding, we performed 2D WAXS measurements on monodomain LCE, LCE-I, LCE-D2%, LCE-D4%, LCE-DI2%, LCE-DI4%. Even though all of them shows two diffuse arcs implying monodomain character but intensity distribution within those arcs gets broader with increasing nps concentration. This result goes well along with the thermal response of these composites. Overall, the results imply that nps impede the reorientation of LC polymer chains along the stress direction in step-2 of the synthesis procedure.

Bilayer Studies

Film transfer technique: For preparing polymeric LCE bilayers, PS films of different thicknesses are prepared by spin-casting a 0.25-5 wt. % PS solution (Mw=191 kg/mol, polydispersity=1.02, Polymer Standards Service-USA Inc) onto a UV-ozone cleaned silicon substrate. To transfer the PS film onto the LCE substrate, the LCE was gently placed on top of the PS film, immersed in water at a fixed temperature for 10 hours, and then peeled off and dried under vacuum. This method can be used to prepare LCE-PS bilayers with different PS film thicknesses and at different preparation temperatures.

As control experiments, LCE bilayers were prepared with both wrinkling pattern parallel and perpendicular to director. This was achieved just by varying the system temperature at film transfer step. For preparing bilayers with wrinkling pattern perpendicular to director, film transfer step was performed at 5-6° C. and gradually temperature was brought up to room conditions. At low temperatures LCE order parameter increases and it expands along the director. After film transfer step when temperature is increased the reverse is true and there is compressive stress along the director. This caused wrinkles to form perpendicular to the director (FIG. 23). Conversely, for preparing bilayer samples with wrinkling pattern parallel to director, film transfer step was done at higher temperatures (40-50° C.).

Another way of preparing bilayers having wrinkles along director at room conditions is by thermal annealing approach. In this approach film transfer step is performed at room conditions and increase system temperature up to the Tg (105° C.) of the PS film. Surface wrinkles oriented perpendicular to the nematic director appear at temperatures below the Tg, but upon annealing the sample near the Tg of PS, surface wrinkles are 'erased' due to viscoelastic flow of the PS film. The surface becomes uniform after annealing for approximately 30 minutes, and on subsequent cooling surface wrinkles reappear oriented parallel to the nematic director. Also as-prepared LCE bilayer samples have some extent of residual stress. This may have been introduced while transferring thin polymer film onto the LCE surface via film transfer technique or during handling of LCE. Residual stress in coatings can either be tensile or compressive and is generally inevitable. They arise due to mismatch in strains during the deposition process. Earlier investigations have shown that residual stresses can cause debonding and even cause through-thickness cracks within the films. The presence of residual stress may also affect film properties including mechanical, optical. Thermal annealing step makes the residual stress present earlier in the coating to disappear. This is due to viscoelastic flow of the stiff PS film above Tg.

One drawback of this approach is that in case of monodomain LCEs large temperature variations are associated with large strains that can cause cracking in stiff polymeric thin films. To overcome this, we slightly modified our earlier thermal annealing procedure to solvent+thermal annealing. In this approach, LCE bilayer samples were thermally annealed at low temperatures (40-50° C.) under the presence of solvent vapor. Slightly elevated temperatures induce the required strain in the bilayers and solvent vapors brings the top polymer film in molten state. Then using vacuum, solvent vapors are removed causing polymer film to become stiff again and system temperature is then gradually lowered up to room temperature. This causes wrinkles to appear parallel to director. Incorporating solvent vapors in thermal annealing approach effectively reduces the Tg of polymer annealing. Choice of solvent will vary with different bilayers, for current study dichloromethane solvent was used. This approach allows us to avoid large temperature changes and also get rid of residual stresses.

Random Wrinkling Instability

As a control experiment for cell culture studies, we also prepared bilayer samples with random wrinkling pattern. This was accomplished by preparing PS-PDMS bilayers via film transfer technique and thermal annealing approach. In this approach film transfer step is performed at room conditions and increase system temperature few degrees above the Tg (105° C.) of the PS film. At T>Tg, the surface becomes uniform after annealing for approximately 30 minutes due to viscoelastic nature of PS film. Also at elevated temperatures PDMS expands isotropically with thermal expansion coefficient of 0.00031 K−1. Then on subsequent cooling two phenomena occurs at the same time (i) PDMS contracts isotropically and (ii) at T<Tg (105° C.) PS film transforms from molten state to crystalline state. As a results of these two process, PS-PDMS bilayer exhibits random wrinkling pattern (FIG. 24). This is a relatively straightforward approach and also by changing PS film thickness random wrinkling pattern with different wavelengths can be obtained.

Dynamic Wrinkling Instability

Dynamic wrinkling instability in LCE composites is accomplished by coating thin PS film on conductive LCE surface and then applying electric field. When electric field is ON, LCE order parameter decreases (as discussed before) and wrinkles appear orienting perpendicular to the director. But when field is OFF, reverse is true i.e. wrinkles disappear. Wavelength and amplitudes of wrinkles depend on both polymer film thickness and strain induced in the system due to LCE electro-mechanical expansion.

Reversible LCE Electromechanical Response

Reversible electromechanical response of CB-LCE composite prepared via immersion+dispersion approach was investigated. The contraction and expansion of LCE composite along the nematic director was recorded under applied electric field for a period of ~18 hours (FIG. 26(a)). A signal was applied to LCE composite with 10 s ON and 10 s OFF time period (FIG. 26(b)). An electric field signal of 40V, 90 Hz and 10 ms pulse width generated by Myopacer (FIG. 26(c)).

LCEs for Dynamic Cell Culture

Materials and Methods

Materials:

Poly(methylhydrosiloxane) (PHMS) was purchased from Gelest and used as received. Reactive liquid crystal 4-methoxyphenyl 4-(3-butenyloxy) benzoate and catalyst dichloro(1,5-cyclooctadiene)platinum(II) were purchased from TCI America and used as received. The crosslinker (1,4-di(10-undecenyloxy)benzene) was synthesized as previously described. Collagen Type I (Rat tail) was purchased from Corning at a concentration of 3.4-3.6 mg/mL and diluted to 50 μg/mL in 0.02 N acetic acid. Laminin was purchased from Sigma Aldrich at a concentration of 1 mg/mL and diluted to 10 μg/mL in 1× Dubelcco's Phosphate Buffered Solution (DPBS) purchased from Corning. Fibronectin (Bovine Plasma) was also purchased from Sigma Aldrich at a concentration of 1 mg/mL and diluted in DPBS to a concentration of 5 μg/mL. Room Temperature Vulcanized medical grade silicone adhesive Silibione MED ADH 4100 was used to adhere LCEs to heaters. PDMS was prepared using Sylgard 184 silicone elastomer kit from Dow Corning at the recommended 10:1 weight ratio of monomer: curing agent. Before use, PDMS elastomers were washed by immersion in dichloromethane to remove unreacted oligomer, followed by air drying. All solvents were purchased from commercial suppliers and used as received. Resistive Kapton flexible heaters were purchased from Omega. Resistive heaters have a heating power of 10 W/in$^2$ and dimensions of 1"×1" (KHLV-101/10-P) or 0.5"×2" (KHLV-0502/10-P).

Preparation of LCE Elastomers:

4-Methoxyphenyl 4-(3-butenyloxy) benzoate (166.2 mg, 0.557 mmol), 1,4-di(10-undecenyloxy)benzene (12.8 mg, 0.0310 mmol) and polymethylhydrosiloxane (40 mg, $M_w$=2300 g/mol) were dissolved in 0.4 mL anhydrous toluene along with 15 microliters of a 1 wt % solution of platinum catalyst dichloro(1,5-cyclooctadiene)platinum(II) in dichloromethane. The reaction mixture was added to a rectangular Teflon mold (3 cm×2 cm×1 cm) and heated to 60° C. for 15 to 20 minutes with gentle agitation. Next, the partially crosslinked elastomer was cooled by briefly immersing the Teflon mold in liquid nitrogen, and then the LCE was carefully removed from the Teflon mold. The sample was cut to the desired dimensions and hung vertically with 6 g of weight attached to the opposite side of the LCE. The LCE was hung under load at room temperature for at least 5 days during which the crosslinking reaction completed and the LCE network was aligned. After completion of the crosslinking reaction, the LCE was immersed in toluene to remove unreacted material and then dried in air.

Modification of LCEs for Cell Attachment:

To enhance cellular attachment, the top surface of the LCE was modified by a combination of UV ozone and plasma cleaning, coating of the top surface with an inert polystyrene or gold film, and deposition of a protein layer. In a typical procedure, LCEs were cleaned by oxygen plasma (Model 1020 Fischione Instruments Plasma Cleaner) for 20 s and then coated with a 30 nm layer of gold by sputtering (Denton Desk V sputter system). The samples were then cleaned by UV ozone for 10 min (Jelight, Model 42 UVO cleaner) and soaked in 70% alcohol before a solution of collagen type I with a concentration of 50 µg/ml in 0.02 N acetic acid was applied to the gold-coated LCE surface. A drop of the collagen solution was placed on the LCE to cover just the surface. This was left for 2 hours at room temperature or overnight at 4° C. Afterwards the LCE was preconditioned in an incubator at 37° C. and 5% $CO_2$ for a minimum of 1 hour before cell seeding. In modified procedures, a 1 mg/mL solution of fibronectin or a 10 µg/mL solution of laminin was deposited on the LCE instead of collagen. Also, as an alternative to gold, a thin polystyrene (PS) film can be deposited on the LCE surface by spin-casting onto silicon and transferring the PS film to the LCE surface, as described previously.

Cell Culture with Neonatal Rat Ventricular Myocytes:

Neonatal rat ventricular myocytes (NRVM) were harvested from freshly dissected ventricles of 1- to 3-day-old Sprague-Dawley rats using an isolation kit (Cellutron, Highland Park, N.J.). Cells were isolated using the Cellutron myocyte isolation protocol. After isolation, cells were resuspended in high-serum plating media (Dulbecco's Modified Eagle Media (DMEM), 17% M199, 10% horse serum (HS), 5% fetal bovine serum (FBS), 100 units/mL penicillin and 50 mg/mL streptomycin) and plated on top of LCE substrates prepared as described above at a density of 100,000-600,000 cells/cm$^2$. Around 18 hours later, cells were transferred to low serum maintenance media (DMEM, 18.5% M199, 5% HS, 1% FBS and antibiotics). LCEs were then subjected to cyclic heating. Resistive heaters were turned on and off through the use of a Myopacer (Ionotopics) field stimulator and time relay. The system can supply AC (0.010-99 Hz) voltages in the range of 0-40 V with pulse durations (equal on and off times) of 0.6 s-24 h. Cell cultures were maintained inside an incubator at 37° C. and 5% $CO_2$ and fresh maintenance media was added every 2-3 days. All culture media was purchased from Invitrogen and sera were purchased from Gemini BioProducts.

Cell Staining and Analysis:

To determine the cell attachment and viability, the cells were stained using a viability/cytotoxicity assay kit from Biotium (product number 30002-T) and left at room temperature for 30 min. They were then imaged and counted using Image J (NIH) cell counter. To outline the membrane of the cell, the cells were stained using Calcein AM (Biotium). For nuclei staining, the cells were covered with VectaShield DAPI-containing mounting medium (Vector Labs) before being imaged under a fluorescent microscope (Lieca). All cell count numbers reported are over a 0.36 mm$^2$ area.

Results and Discussion

Our experimental configuration for cell culture studies with LCE substrates is shown in FIG. 27. Monodomain liquid crystal elastomers were prepared through a two-step method crosslinking method, with some modifications (see Experimental section for detailed procedure). The LCEs prepared for this study were polysiloxane based side-group liquid crystal elastomers, and the final samples were rectangular with length L of 10 mm, width W of 5 mm and thickness H of 0.5 mm. For use in cell culture, the LCE surface was modified to enhance cell attachment, placed on top of a resistive heater and immersed in cell culture media. The entire system was kept in a temperature controlled incubator held at 37° C. Heat supplied transiently to the bottom LCE surface result in bulk LCE temperature changes, which lead to reversible, uniaxial elongation and contraction of the LCE sample during cell culture. The heating power and on/off pulse durations were tuned to achieve a desired strain and frequency and to minimize ambient heating. Below, we discuss the shape-response of LCEs in water before presenting the results of culturing neonatal rat ventricular myocytes (NRVM) on shape-responsive LCEs.

The response of the LCEs to transient heating can be predicted through simple physical arguments based on energy conservation and known physical properties of the LCEs. The LCE samples were rectangular with a thickness 500 µm and total volume V of 0.025 cm$^3$. The density, heat capacity, and thermal conductivity of the LCE is approximated to be that of poly(dimethylsiloxane) (PDMS), which has a density ρ of 0.97 kg/m$^3$, heat capacity $C_p$ of 1460 J/kg K and thermal conductivity k of 0.15 W/m K. LCEs contract spontaneously by 35% when heated from room temperature to the nematic-to-isotropic transition temperature ($T_{NI}$), and the LCEs studied have a $T_{NI}$ of approximately 75° C. measured by differential scanning calorimetry. Based on these values, the amount of heat required to raise the bulk temperature of the LCE from 37° C. to the $T_{NI}$ (75° C.) is ρ $C_p \Delta T$, or approximately 1.8 J. Thus, small amounts of heat, supplied locally to the LCE, can provide significant bulk temperature changes and macroscopic shape-changes in the LCE.

Under transient heating, the bulk temperature of the LCE will vary as the external heating source is turned on and off and heat is dissipated to the surroundings. Assuming that heat is dissipated quickly at the surface of the LCE in contact with water, the characteristic time scale for bulk temperature changes (and therefore sample strains) is set by thermal diffusion through the thickness of the LCE, $\sim \rho C_p H^2/k$, or roughly 2 s for the present samples. Thinner LCE samples or LCEs with higher thermal conductivities respond more quickly. This simple analysis demonstrates that local heating of LCEs can produce bulk temperature changes and therefore macroscopic sample strains (up to 35%) on timescales on the order of ~2 s with low amounts of heat (~1.5 J) dissipated to the surroundings per cycle. These strains and timescales are comparable to the strains and frequencies used to align cells by mechanical deformation of a substrate or scaffold.

As shown in FIG. 27, monodomain LCEs placed on a resistive heater with 5-20 W heating power and 1-10 s pulse duration contract and elongate reversibly in water. LCEs reach steady state after several minutes of cycling and exhibit fully reversible strain in response to transient heating. The magnitude of the reversible strain depends on both the heating power and the pulse duration. Higher heating powers or longer pulse durations result in larger changes in the bulk LCE temperature and therefore larger strains. In all cases, the strain is fully reversible.

To gain a more quantitative understanding of the reversible shape response of LCEs under water, the reversible strain was measured for varying pulse durations and heating powers. The response of LCEs to cyclic on/off heating pulses at varying heating powers is shown in FIG. 28. Strains were measured by recording videos of the shape response and analyzing the images to measure sample strains. For low heating powers, the reversible strain was roughly 5% even for long pulse durations, but at higher heating powers reversible strains as high as 35% were recorded. For low pulse durations (0.6 s) all LCEs exhibited less than 1% strain. At these short pulse durations, heat was dissipated quickly and the bulk LCE temperature remained relatively constant. At 1 s pulse durations, up to 4% reversible strain was achieved with 20 W heating power. In comparison to experiments performed in water at 5 W, samples in air exhibited higher strain values in response to cyclic heating. This is expected due to the faster heat dissipation in water, which results in lower bulk temperature fluctuations in LCEs. These measurements demonstrate that LCEs can respond reversibly in water, and the response time and strain can be tuned by varying the heating power and pulse duration. Videos demonstrating the response of LCEs in air and under water on top of resistive heaters are shown in supplementary videos available online.

The LCE bulk and surface temperature and the temperature in the ambient media are important for the proposed application. Variations in the bulk LCE temperature give rise to macroscopic strains (shown in FIG. 28), and, ideally, the surface and media temperatures should remain close to ambient. The LCE bulk temperature was monitored by incorporating a thermocouple in the LCE. We also monitored the temperature near the surface of the resistive heater, near the top surface of the LCE, and in the media far from the heater and LCE. As shown in FIG. 28 for 12 W heating power, the temperature near the resistive heater varied substantially for pulse durations of 5 s and greater, by up to 20° C. between on and off pulses. The LCE bulk temperature fluctuated by almost as much at long pulse durations, but at 5 s pulse durations and shorter the bulk LCE temperature varied by only roughly 3° C. The temperature near the LCE surface fluctuated substantially less than the bulk LCE temperature, even at long pulse durations. This indicates that heat dissipation at the LCE surface was effective at maintaining a relatively constant temperature at the surface where cells can attach to the LCE. While the average temperature near the LCE surface was measured to be 5-10° C. elevated relative to ambient temperature (25° C.), the temperature of the water in the petri dish far from the LCE surface and resistive heaters remained at ambient. Data for 5 W and 20 W heating powers are provided in the Supporting Information FIGS. 34 and 35, respectively.

The results presented above indicate that LCEs may be effective for cell culture at lower pulse durations and heating powers. In order to implement LCEs for use in cell culture, the top surface was modified to allow cell attachment. Polysiloxane elastomers like poly(dimethylsiloxane) (PDMS) and LCEs have low surface and adhesion energies. A series of coatings was tested on PDMS elastomers to determine the most viable for myocyte attachment. PDMS was used as the test substrate because it is readily available, easily synthesized in large quantities and has a similar molecular chemical structure to our LCEs. To modify the surface, a thin layer of polystyrene (PS) was deposited on PDMS, the surface of the PDMS-PS bilayer was subjected to UV-ozone or plasma cleaning and finally the treated bilayer was coated with one of three different proteins: collagen, fibrinogen or laminin. These treated PDMS-PS elastomers were then used to culture neonatal rat ventricular myocytes (NRVM). Cell viability was analyzed by live-dead assays (calcein AM staining). Tissue-culture plastic and untreated PDMS-PS elastomers were used as positive and negative controls, respectively.

As shown in FIG. 30, protein layers exhibited improved NRVM viability compared with PS-PDMS negative control but reduced viability compared with tissue-culture plastic. No significant difference is observed in NRVM viability between the different protein samples, but our experiments indicate reduced cell attachment on surfaces treated with fibrinogen and laminin compared with collagen. Collagen was used as the protein coating for all studies described below.

Next, we tested cell attachment and viability on LCEs compared with PDMS. As an alternative to PS, which is a suitable thin film coating but tedious to apply, we coated elastomers with a thin, inert gold layer (30 nm). Gold was easily deposited on multiple samples simultaneously using a sputter coater. Next, the surfaces were cleaned by UV-ozone, and collagen was deposited on the surfaces. Since silicone elastomers are known to undergo time-dependent changes of surface chemistry, we tested the effect of applying collagen immediately after UV-ozone cleaning and after waiting 16 h before applying collagen to the surface. NRVM were then cultured on the substrates, and the resulting surfaces were analyzed for cell viability and attachment.

Both PDMS and LCE elastomers modified by gold and collagen treatment exhibited high NRVM viability (see FIG. 31). A larger number of cells were found to attach to LCEs compared with PDMS, and a drop in cell attachment was observed for both elastomers when waiting 16 h in between UV-ozone treatment and collagen deposition. This suggests that surface chemistry changes over this time period may affect collagen deposition on the elastomer surfaces. Representative live-dead assays from both PDMS and LCEs are shown in FIG. 32, showing high NRVM viability greater than 95%.

Based on the results above, which indicated myocytes adhered to surface-modified LCEs and LCEs exhibited reversible strain under cyclic heating, we tested cell attachment, viability, and orientation when deposited on LCEs subjected to cyclic heating. It should be noted that the deposition of a thin gold layer does not affect the macroscopic strain of the LCEs but can affect the surface topography. Gold-coated LCEs are expected to exhibit aligned surface wrinkles that disappear and reappear depending on sample strain. This reversible surface wrinkling in LCEs has been previously demonstrated by our laboratory.

Based on the strain and temperature measurements conducted (FIGS. 2 and 3), we conducted cyclic heating experiments at 12 W heating power. This avoids excessive heating of the LCE and large temperature variations while still achieving significant (5%) sample strains. The pulse duration chosen was 6.5 s. NRVM were cultured on LCEs under static conditions for 18 hours, and then cyclic heating was initiated continuously for 3 days. After 4 days, cells were stained for analysis.

As shown in FIG. 33, cells successfully attached on LCEs subjected to cyclic heating. The density of cells attached to the surface was substantial, even under cyclic heating. Viability and total cell counts were difficult to quantify precisely due to the high density of cells, but nuclei staining confirmed that cells attached to the surface, some of which are elongated and some spherical in shape. Some regions of the LCEs showed evidence for myocyte alignment along the primary strain direction (horizontal), but other regions on the surface did not exhibit significant cell alignment. It is unclear whether this is due to non-uniform sample strain, inhomogeneities on the surface, or some other disturbance during culturing and analysis. Some samples also showed evidence for cell connectivity and network formation (see Supporting Information FIG. 36).

This results presented demonstrate that LCEs can be implemented as shape-responsive substrates for cell culture in a simple device configuration. Heat can be used as a stimulus to produce reversible shape changes of 1-5% and frequencies of 10 Hz or smaller. The cell culture data presented indicates that cells remain viable and attach to the surface of the LCE during cyclic heating/straining.

While a relatively simple device configuration was used in the present work, the same procedures reported here can be combined with innovative strategies for achieving a stimulus-response in LCEs. For example, conductive LCE nanocomposites can respond directly to electrical stimulation and localized heating. Dye-doped LCEs or carbon-nanotube LCE nanocomposites respond to light and/or IR-radiation, enabling remote activation with no physical contact to a heating element or electrode. Other opportunities include using the combination of surface wrinkling with macroscopic strains to engineer aligned cellular constructs.

Other Studies

Additionally, techniques and protocols for measuring the force response of cardiac sheets, fibers and constructs, as well as the response to physiologic conditions such as the concentration of inotropes, increasing strain, calcium concentration and frequency of electrical pacing were developed. These parameters give an overview indication of functional response of cells when implanted as shown in FIG. 9. A technique for the measurement of electrical connectivity through imaging of a voltage sensitive dye, allowing calculation of a depolarization wave speed as shown in FIG. 10 was also developed. In general, slower depolarization waves through a patch would increase the probability of the induction of arrhythmias.

Human cardiomyocytes from a small section (1 cm$^3$) of human right ventricular outflow tract tissue using a collagenase and hyaluronidase digestion based on published techniques was successfully isolated. This yielded 675,000 cells and spontaneous beating was observed immediately after isolation. In order to find optimal culture conditions, cells were maintained in six different media. Cells cultured in a media consisting of M199 media with 2 mg/ml bovine serum albumin, 2 mM L-carnitine, 5 mM creatine, 5 mM taurine, 0.5 M insulin, 0.1 nM T3 (triiodothyronine, a thyroid hormone), 5% fetal bovine serum, penicillin and streptomycin maintained the highest viability and spindle-like morphology over 14 days (FIG. 11). This media had previously been shown by others to maintain human atrial cardiomyocytes for longer than 2 weeks.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

It is contemplated that any instance discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A cell culture substrate comprising:
    a shape-responsive layer comprising a liquid crystal mesogen, a crosslinker and a polymer; and
    a cell-adhesion layer comprising a material selected from the group consisting of gold, polystyrene, collagen, fibronectin, laminin, and combinations thereof.

2. The substrate of claim 1 wherein the liquid crystal mesogen is 4-methoxyphenyl 4-(3-butenyloxy) benzoate and the polymer is polymethylhydrosiloxane, and wherein the cell-adhesion layer comprises gold and collagen.

3. The substrate of claim 1 wherein the shape-responsive layer further comprises carbon black nanoparticles.

4. The substrate of claim 3 wherein the carbon black nanoparticles are dispersed throughout the shape-responsive layer with an increased concentration of carbon black nanoparticles at an edge of the shape-responsive layer.

5. The substrate of claim 3 wherein the substrate possesses an electrical resistivity of from about 0.1 Ω·m to about 10.0 Ω·m.

6. The substrate of claim 3 wherein the substrate possesses an elastic modulus of from about 3 kN to about 9 kN.

7. The substrate of claim 3 wherein the substrate possesses a thermo-mechanical strain from about 1% to about 27%.

\* \* \* \* \*